United States Patent [19]

Letourneur et al.

[11] Patent Number: 5,019,269

[45] Date of Patent: May 28, 1991

[54] POLYMERS DERIVED FROM CROSSLINKED POLYSTYRENES AND DEXTRANS, THEIR METHODS OF PREPARATION AND THEIR APPLICATIONS FOR THE ANALYSIS AND PURIFICATION OF MOLECULES OF BIOLOGICAL ORIGIN

[75] Inventors: Didier Letourneur, Aulnay; Colette Douzon, Paris; Véronique Migonney, Eaubonne; Daniel A. Muller, Soisy sus Montmorency; Marcel Jozefowicz, Lamorlaye, all of France

[73] Assignee: Centre National de la Recherche Scientifique, Paris, France

[21] Appl. No.: 497,560

[22] Filed: Mar. 21, 1990

Related U.S. Application Data

[62] Division of Ser. No. 235,113, Aug. 22, 1988, Pat. No. 4,950,712.

[30] Foreign Application Priority Data

Aug. 21, 1987 [FR] France .................. 87 11813

[51] Int. Cl.$^5$ ............................................. B01D 15/08
[52] U.S. Cl. .................... 210/635; 210/656; 210/198.2; 210/502.1; 530/413; 530/417; 536/127
[58] Field of Search ............ 210/635, 656, 198.2, 210/502.1; 525/54.2, 333.3, 333.6; 536/24, 28, 112, 127; 530/413, 417

[56] References Cited

U.S. PATENT DOCUMENTS 4,659,774 4/1987 Webb .................................. 525/54.2
4,780,504 10/1988 Buendia ............................. 525/54.2

*Primary Examiner*—Ernest G. Therkorn
*Attorney, Agent, or Firm*—Bierman and Muserlian

[57] ABSTRACT

These resins derived from a crosslinked styrene (co)-polymer, or from a crosslinked dextran, comprise a (co)-polymer chain which is substituted with one or more groups, which may be identical or different, belonging to the following categories: $-Z-A_1$; $-Z-A_2$; $-Z-A_1-Z'-A_2$; $-Z-A_1-A_3-A_2$; $-Z-A_1-A_4$, where Z=spacer chain, Z'=linking chain, $A_1$=phosphate residue, $A_2$=residue of purine or pyrimidine base, $A_3$=sugar residue and $A_4$=residue of a molecule participating in the polar structure of various phospholipids. These resins are applicable for the analysis and purification of molecules of biological origin, in particular as a stationary phase in ion-exchange and affinity chromatography, especially for carrying out the fractionation of protein mixtures. Their interaction with proteins, in particular the anti-DNA and anti-phospholipid antibodies present in the serum of patients suffering from SLE, makes them applicable to operations for the selective purification of the different types of antibodies developed by Lupus patients.

12 Claims, 7 Drawing Sheets

ALBUMINE (pH=5)

MYOGLOBINE, CYTOCHROME C (pH=7.6)

POLYMERS DERIVED FROM CROSSLINKED POLYSTYRENES AND DEXTRANS, THEIR METHODS OF PREPARATION AND THEIR APPLICATIONS FOR THE ANALYSIS AND PURIFICATION OF MOLECULES OF BIOLOGICAL ORIGIN

PRIOR APPLICATION

This appliction is a division of U.S. patent application Ser. No. 235,113 filed Aug. 22, 1988, now U.S. Pat. No. 4,950,712.

FIELD OF THE INVENTION

The present invention relates to new resins which consist of polymers resulting from the modification of polymers capable of being used as chromatographic supports, which are crosslinked polystyrenes and dextrans; the present invention also relates to the preparation of these resins, as well as to their applications for the analysis and purification of molecules of biological origin, in particular as a stationary phase in ion-exchange and affinity chromatography, especially for carrying out the fractionation of protein mixtures. In addition, their interaction with proteins, in particular the anti-DNA and anti-phospholipid antibodies present in the serum of patients suffering from SLE, makes them applicable to operations for the selective purification of the different types of antibodies developed by lupus patients.

These new resins according to the invention have the novel feature of containing substituents that mimic the chemical sites of DNA and of some phospholipids, and they possess a much larger ion-exchange capacity than traditional chromatographic supports. They conventionally take the form of particles in the case of crosslinked polystyrenes, or of gels in the case of crosslinked dextrans, having at their surface, in a statistical distribution, the following different components, namely, purine and pyrimidine bases, pentoses, phosphates and phospholipid constituents, bound independently or in an associated manner, to the polystyrene or dextran units with spacer arms having variable length and chemical nature, it being possible for high degrees of substitution to be obtained. The possible presence of phosphorylated groups makes these resins especially advantageous in ion-exchange chromatography. Thus, the resins according to the present invention, bearing phosphate groups, which could not hitherto be grafted in large amounts onto the traditional stationary phases, have acid-base, and hence ion-exchange, properties that are quite markedly different from those of the usual supports.

Moreover, the resins based on crosslinked polystyrenes show the additional advantage of having the excellent mechanical qualities of the base polymer, making them usable in high performance liquid chromatography (HPLC).

BACKGROUND OF THE ART

The chromatographic supports which have been developed hitherto in ion-exchange chromatography are most frequently based on natural polymers, modified in order to bear groups permitting the exchange of cationic proteins (carboxymethyl, sulfopropyl groups) or anionic proteins (aminoethyl, diethylaminoethyl groups). However, these supports are gels which permit use only at low pressure, thereby considerably limiting their use on the industrial scale. In effect, their low mechanical strength limits, or even prohibits, their use in HPLC and, accordingly, their industrial value.

To remedy these drawbacks, supports which, by virtue of their crosslinking, possess good mechanical properties, that is to say good rigidity, have already been sought for these applications. Among the polymers which have thus been proposed, polyacrylamide, trisacrylic polymer, poly(hydroxymethyl methacrylate) and vinyl polymers may be mentioned. However, the chemical modifications which have been performed for the purpose of endowing the base polymers with the character of an ion-exchange support often remain difficult, and the degrees of substitution obtained are generally low.

Thus, supports based on crosslinked polystyrene with a content of the order of 2% of divinylbenzene possess excellent mechanical qualities, but their strongly hydrophobic nature has, to date, limited their use in protein chromatography. In order for such a support to be usable in the exchange chromatography of products of biological origin, it is necessary for it to be heavily substituted with units that are both hydrophilic and ionizable.

GENERAL DESCRIPTION OF THE INVENTION

The functional hydrophilic polystyrenes (and styrene copolymers) of the invention provide an answer to the problems posed. It has become apparent, in effect, that such resins are still usable under elution conditions in high-performance liquid chromatography, since they withstand pressures in the region of 200 bars without modification.

DETAILED DESCRIPTION

The subject of the present invention is, in the first place, a polymer derived from a crosslinked styrene polymer or copolymer or from a crosslinked dextran, in which the chain of the base polymer or copolymer is substituted with one or more groups, which may be identical or different, belonging to the following categories:

—Z—A$_1$;
—Z—A$_2$;
—Z—A$_1$—Z'—A$_2$;
—Z—A$_1$—A$_3$—A$_2$;
—Z—A$_1$—A$_4$ where:
Z denotes a spacer chain;
Z' denotes a linking chain;
A$_1$ denotes a phosphate residue;
A$_2$ denotes the residue of a purine base or of pyrimidine base;
A$_3$ denotes a sugar residue; and
A$_4$ denotes a residue of a molecule participating in the polar structure of the various phospholipids.

The spacer chain Z is, in particular, chosen from the residues:

—(CH$_2$)$_n$—, n equalling from 1 to 6, optionally made hydrophilic by the replacement of at least one H by an OH; or
—SO$_2$—NH—(CH$_2$)$_m$—, m equalling from 1 to 6, the residue —(CH$_2$)$_m$— optionally being made hydrophilic by the replacement of at least one H by an OH; and in the case of the modification of a crosslinked dextran, also

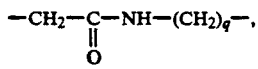

$q$ equalling from 1 to 6, the residue —(CH$_2$)$_q$— optionally being made hydrophilic by the replacement of at least one H by an OH.

In particular, the following residues may be mentioned as spacer chains Z: —CH$_2$—; —(CH$_2$)$_2$—; —(CH$_2$)$_3$—; —SO$_2$—NH—(CH$_2$)$_{2 or 3}$—; —SO$_2$—NH—CHOH—; and —SO$_2$—NH—CH$_2$— CHOH—CHOH—; and in the case of the modification of a crosslinked dextran, also,

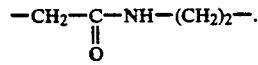

As regards the linking chain Z', this consists, in particular, of the chain —(CH$_2$)$_p$, p equalling from 1 to 6, the residue —(CH$_2$)$_p$ optionally being made hydrophilic by the replacement of at least one H by an OH.

As regards the residue A$_2$, the residues of the major purine bases, namely adenine and guanine, as well as the residues of the major pyrimidine bases, namely cytosine, thymine and uracil, may be mentioned by way of examples.

The residue A$_3$ denotes, in particular, a sugar residue, linked via its —CH$_2$— group to the phosphate residue; by way of example, a pentose residue may be mentioned, in particular the D-ribose (or 2-deoxy-D-ribose) residue of formula:

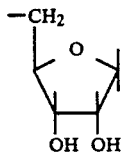 (H)

As regards residue A$_4$, this denotes in particular, an esterified molecule of choline, of ethanolamine, of serine, of glycerol or of inositol.

One of the base polymers, which is modified according to the present invention, is a styrene homo- or copolymer which may be defined as a polymer based on a mixture of base monomers comprising, for 100 parts by weight, 50–100 parts by weight of styrene, optionally substituted, such as α-methylstyrene, and 0–50 parts by weight of at least one ethylenically unsaturated copolymerizable monomer chosen, in particular, from acrylic monomers such as lower alkyl acrylates and methacrylates, lower alkoxy acrylates, acrylonitrile, acrylamide, lower hydroxyalkyl acrylates, lower hydroxyalkyl methacrylates, acrylic acid and methacrylic acid. In addition, these styrene polymers are crosslinked, that is to say a traditional crosslinking monomer, chosen, in particular, from polyvinylbenzenes, such as divinylbenzene, has been added to the starting monomers, in a quantity which can range up to 5 parts by weight for 100 parts by weight of the said monomers.

According to the invention, styrene homopolymer, which is a traditional support, will preferably be used; that used here was a crosslinked polystyrene with at most 5% by weight, and especially with 2% by weight, of at least one crosslinking monomer, such as divinylbenzene, and which took the form of beads having a size in the region of 50 μm.

In the interest of simplification, styrene homo- and copolymers will be designated in the remainder of the present specification by the term "polystyrene".

The substitution of the polystyrene chain according to the invention is mainly performed at the para position of the benzene ring.

Moreover, according to the present invention, each phenyl group not involved in the crosslinking can contain a substituent as defined above.

The crosslinked polymer which is modified according to the invention, can also be a crosslinked dextran, such as a dextran partially substituted with carboxymethyl groups. The dextrans used can be those crosslinked with epichlorohydrin.

The subject of the present invention is also a method for preparing the polymer derived from crosslinked polystyrene or dextran, as defined above, which method comprises the binding to the base crosslinked polymer or copolymer (polystyrene or dextran), in one or more stages, of a residue —Z—OH or, in the case of the styrene polymer or copolymer, of a residue —Z—X (where X denotes halogen and Z is as defined above), and then (I) in the case where a residue —Z—X has been bound, the reaction of the polystyrene thus modified with a purine or pyrimidine base, in order to form the substituent —Z—A$_2$;

(II) in the case where a residue —Z—OH has been bound,
  (IIa) the phosphorylation of the polymer or copolymer thus modified, in order to form the substituent —Z—A$_1$; and then
  when it is desired to form the substituent —Z—A$_1$—Z'—A$_2$, the reaction of the residue —Z—A$_1$ with a modified purine base represented diagrammatically by the formula:

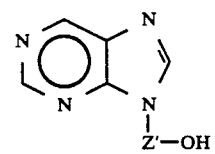 (I)

or with a modified pyrimidine base represented diagrammatically by the formula:

 (II)

when it is desired to form the substituent —Z—A$_1$—A$_3$—A$_2$, the reaction of the residue —Z—A$_1$ with a nucleoside of the formula —A$_3$—A$_2$, resulting from the linking of the nitrogen[9] of a purine base or the nitrogen[1] of a pyrimidine base with the carbon[1'] of a sugar;

when it is desired to form the substituent —Z—A$_1$—A$_4$, the reaction of the group —Z—A$_1$ with a molecule participating in the polar structure of various phospholipids; alternatively (IIb) when it is desired to form the substituent —Z—$A_1$—$A_3$—$A_2$— directly, the reaction of the polymer or copolymer thus modified with a nucleoside monophosphate of the formula $A_1$—$A_3$—$A_2$;

(IIc) when it is desired to form the substituent —Z—$A_1$—Z'—$A_2$, the reaction of the polymer or copolymer thus modified with a converted purine base represented diagrammatically by the formula:

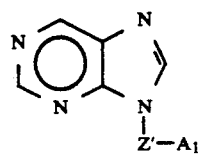

and which is obtained by phosphorylation of the modified purine base of the formula (I), or with a converted pyrimidine base represented diagrammatically by the formula:

and which is obtained by the phosphorylation of the modified pyrimidine base of formula (II); or alternatively (IId) when it is desired to form the substituent —Z—$A_1$—$A_4$, the reaction of the polymer or copolymer thus modified with a phosphorylated residue $A_4$.

In the case where a crosslinked polystyrene is used as a starting polymer:

1) It is possible to begin by binding a radical —$CH_2$—X to the starting polystyrene, by reacting the said polystyrene with a halomethyl methyl ether in the presence of stannic chloride.

2) It is also possible to begin by binding a —$CH_2OH$ radical to the starting polystyrene, by reacting, in the presence of a phase transfer catalyst, the resin obtained as described above, that is to say modified by radicals —$CH_2$—X, with potassium acetate, and then by hydrolyzing the acetate obtained with concentrated potassium hydroxide.

3) It is also possible to begin by binding a —$CH_2$—$CH_2$—OH radical to the starting polystyrene, by reacting the resin, modified so as to bear radicals —$CH_2$—X, with sodium cyanide, in the presence of a phase transfer catalyst, to obtain a substituent —$CH_2$—C≡N;

then by reacting the polystyrene thus modified with hydrochloric acid in an alcoholic medium, in order to obtain a substituent —$CH_2$—COOH;

and then by reducing with diborane, in order to obtain a substituent —$CH_2$—$CH_2$—OH.

4) It is also possible to begin by binding a —$CH_2$—$CH_2$—$CH_2$—OH radical to the starting polystyrene, by condensing an alkyl malonate with the resin containing groups —$CH_2$—X, in order to obtain a substituent:

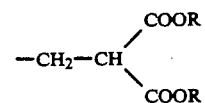

(R being an alkyl residue);

then by hydrolyzing the diester group thereby obtained to give a diacid group, which is subjected to a decarboxylation in acid medium, in order to obtain a substituent —$CH_2$—$CH_2$—COOH;

and then by reducing with diborane in order to obtain a substituent —$CH_2$—$CH_2$—$CH_2$—OH.

5) It is also possible to begin by binding an —$SO_2$—N-H—$(CH_2)_{2 or 3}$—OH radical to the starting polystyrene, by reacting chlorosulfonic acid with the starting polystyrene, so as to obtain a substituent —$SO_2Cl$, and then by reacting ethanolamine or propanolamine with the abovementioned substituent. p0 6) It is also possible to begin by binding an —$SO_2$—N-H—$CH_2$—CHOH—$CH_2OH$ radical to the starting polystyrene, by reacting chlorosulfonic acid with the starting polystyrene, so as to obtain a substituent —$SO_2Cl$;

and then by reacting 3-amino-1,2-propanediol with the abovementioned substituent.

In the case where a crosslinked dextran is used as a starting polymer, it is possible to begin by binding a radical —NH—$(CH_2)_q$—OH thereto, q ranging from 1 to 6, by reaction with a thionyl halide, followed by reaction with an amine of formula OH—$(CH_2)_q$—$NH_2$, or alternatively using a coupling agent, by condensation with the said hydroxylated amine.

The phosphorylation is advantageously carried out using methyl dichlorophosphate, phosphorous acid or phosphorus oxychloride, and in particular using phosphorus oxychloride.

To prepare the modified bases of formulae (I) or (II) in which Z' equals —$CH_2$—$CH_2$—, the base is reacted with ethylene carbonate in the presence of a phase transfer catalyst.

The reaction of the residue —Z—$A_1$ with the modified bases of formulae (I) or (II) is carried out using a coupling agent such as N,N'-dicyclohexylcarbodiimide (DCCI).

Finally, a modified base of formula (Ia) or (IIa) is prepared by phosphorylating the corresponding base of formula (I) or (II), respectively, with $POCl_3$, and the said base of formula (Ia) or (IIa) is then condensed with the substituent —Z—OH using a coupling agent, such as DCCI.

The subject of the present invention is also the use of the polymer derived from a crosslinked polystyrene or dextran, as defined above, as a stationary phase in ion-exchange chromatography, and especially for the fractionation of protein mixtures, and also as a stationary phase in affinity chromatography, for example for carrying out selective purifications of the different types of anti-bodies developed by lupus patients (anti-DNA antibodies, antibodies to circulating coagulants and antiphospholipid antibodies). The purification, by affinity or ion-exchange chromatography of enzymes, coenzymes or enzyme complexes accepting DNA, RNA and nucleotides as substrates may also be mentioned; as well as the purification from various plasma extracts, of blood coagulation factors.

The subject of the present invention is also the use of the polymer derived from a crosslinked polystyrene or dextran, as defined above, for the purification of molecules of biological origin, such as the proteins participating in the process of blood coagulation, and in biological analytical systems such as RIA, ELISA, electrophoresis, one- and two-dimensional immunoelectrophoresis, electrofocussing, and the like. By way of an example, there may be mentioned the assays of the different types of lupus antibodies, and in particular the assay of circulating anticoagulants and/or anti-phospholipids.

DESCRIPTION OF PREFERRED EMBODIMENTS

Figure 1:
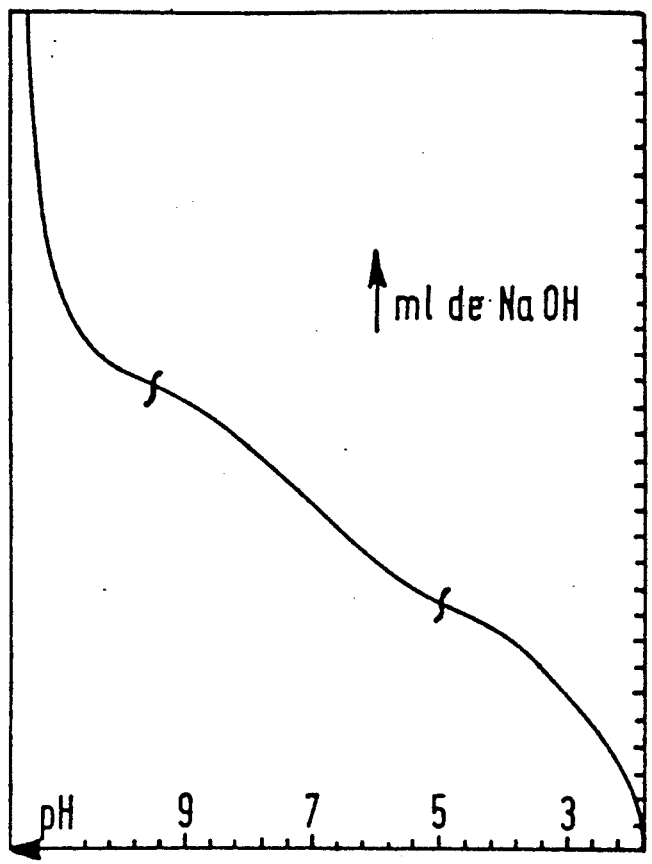
FIG. 1 is a titration curve by sodium hydroxide of a resin substituted by an alkyl-phosphate group and obtained in the same manner as in Example F2 and 1.
Figure 2:
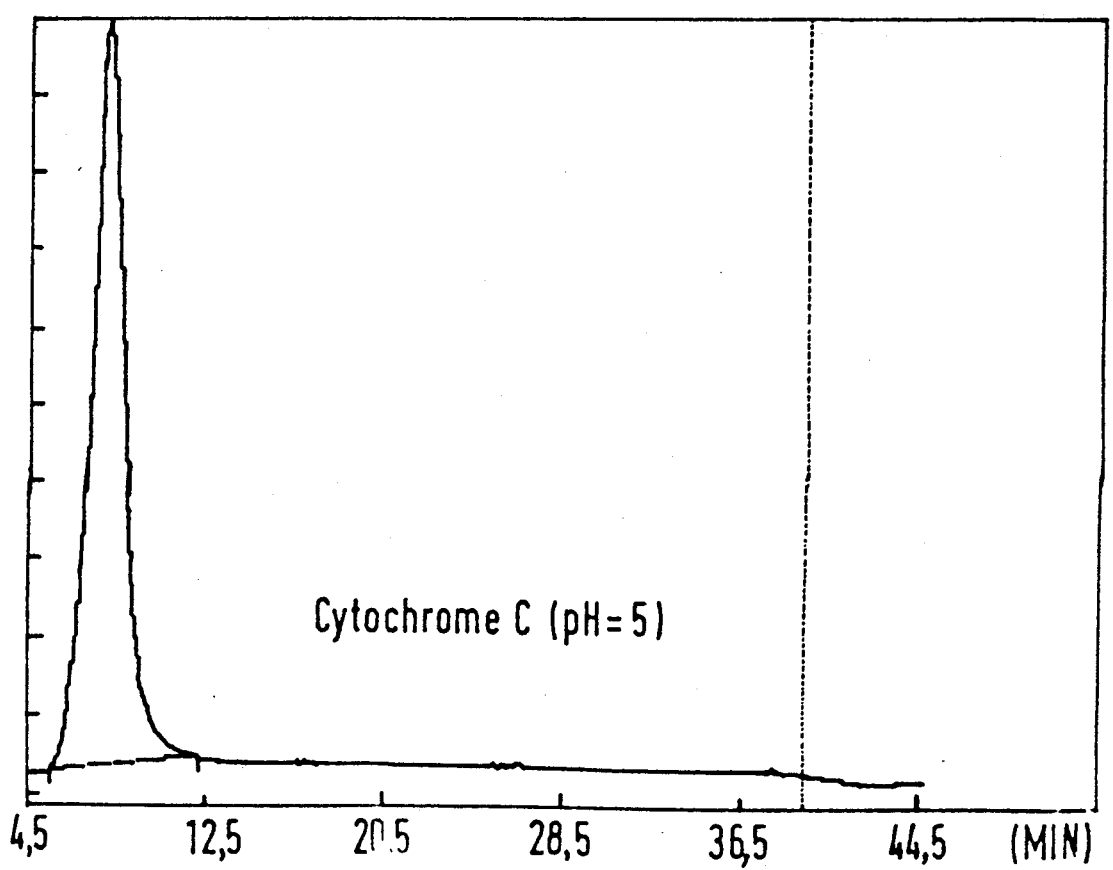
FIGS. 2 to 6 are chromatograms using the resin of Example 8 in a stainless steel column with a HPLC system, of Cytochrome C in different conditions of elution for FIGS. 2 and 3, of Ribonuclease for FIG. 4, of Albumin for FIG. 5 and of Cytochrome C and Myoglobin for FIG. 6.
Figure 3:
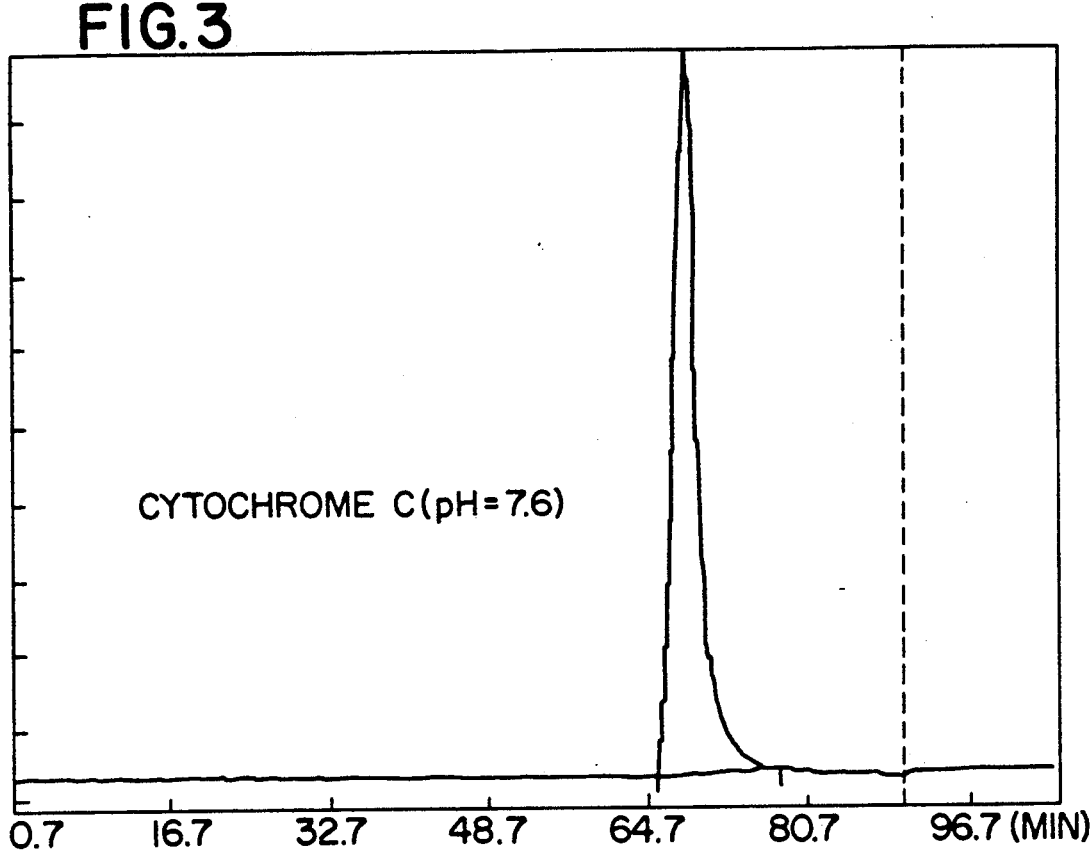
Figure 4:
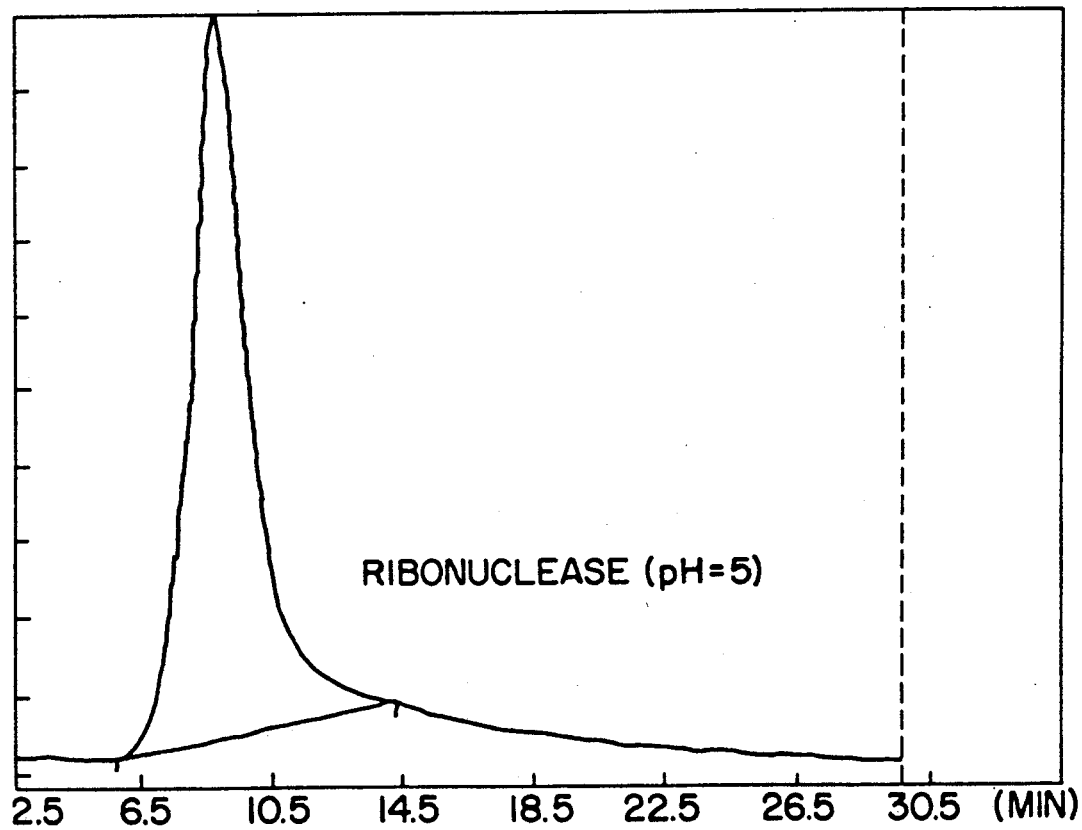
Figure 5:
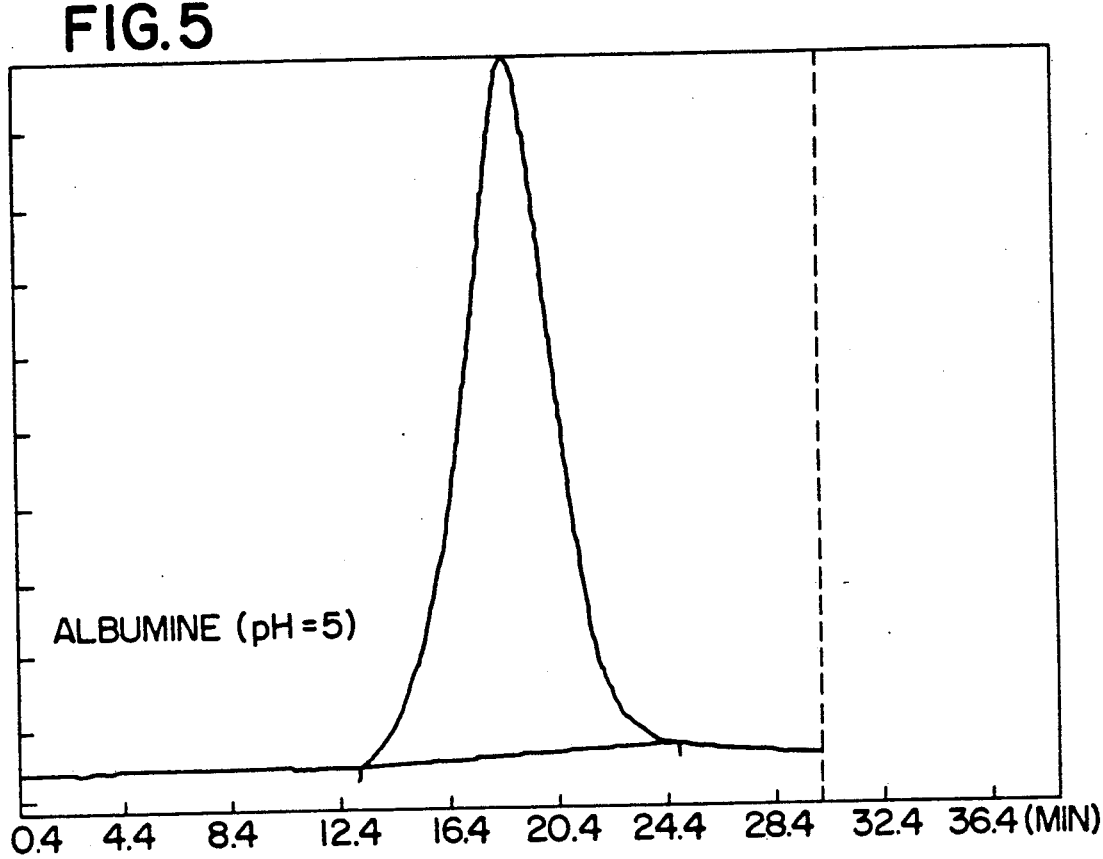

To Illustrate the present invention more clearly, several embodiments will be described below. Examples A to H relate to the preparation of different modified polystyrene resins which are intermediates in the preparation of the resins according to the present invention. Examples 1 to 7 relate to the preparation of different resins according to the present invention. The microanalytical results for each of the resins involved are recorded in Table III, which follows Example 6. Examples 8 to 12 illustrate the different uses of the resins according to the invention.

EXAMPLE A

Preparation of poly(para-chloromethyl styrene)

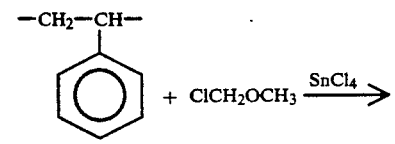

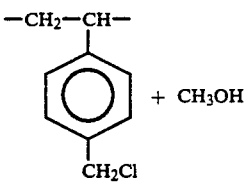

24.5 g (235 meq) of polystyrene (FLUKA) are placed in 250 ml (4,000 meq) of $CH_2Cl_2$ with stirring, for 4 hours. 45 ml (600 meq) of $ClCH_2OCH_3$ and 10 ml (85 meq) of $SnCl_4$ are added at 0° C., and stirring is then maintained, at room temperature, for 2 and a half hours. Next, the mixture is filtered and the resin is left in suspension in $CH_2Cl_2$, then in a 3N HCl (¼)/dioxane (¾) mixture, dioxane/$H_2O$ mixtures with increasing quantities of dioxane, methanol and $CH_2Cl_2$.

The yield is greater than 80%.

This resin PS—$CH_2Cl$ will be used as a basis for many reactions.

TABLE I

| ARGENTIMETRIC ASSAY* PS—$CH_2Cl$ (microanalysis) | | | |
|---|---|---|---|
| Meq/g of —$CH_2Cl$ | 5.1 | 5.3 | 5.8 |
|  | (5.3) | (5.15) | (5.7) |
| % Cl in g/100 g | 18.1 | 18.8 | 20.6 |
|  | (18.8) | (18.3) | (20.1) |
| % Substitution | 77.8 | 81 | 88 |
|  | (81.1) | (78.5) | (86.9) |

*The chlorine content of the resin prepared is determined by assay of the chloride ions liberated by hydrolysis with butylamine. After the suspension has been acidified, the assay is performed using a silver-indicating electrode with a solution of silver nitrate.

butylamine. After the suspension has been acidified, the assay is performed using a silver-indicating electrode with a solution of silver nitrate.

EXAMPLE B

Preparation of poly(para-chlorosulfonyl styrene)

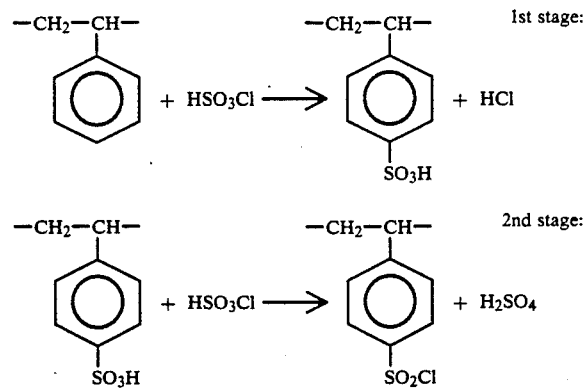

In the remainder of the present specification the symbol PS will replace polystyrene substituted at the para position.

2.6 g (25 meq) of polystyrene (FLUKA) are placed in 125 ml (2,000 meq) of $CH_2Cl_2$ with stirring, for 4 hours, at room temperature. 15 ml (225 meq) of $HSO_3Cl$ are then added and the mixture is left for 1 hour with stirring. The mixture is filtered with $CH_2Cl_2$, then acetone and $CH_2Cl_2$, and the product obtained is used immediately for reacting with ethanolamine, propanolamine or 3-amino-1,2-propanediol.

The total yield is in the region of 80%.

TABLE II

| ARGENTIMETRIC ASSAY* OF PS—SO₂Cl | | |
|---|---|---|
| Meq/g of —SO₂Cl | % Cl in g/100 g | % substitution |
| 3.86 | 13.7 | 78.2 |
| 3.88 | 13.8 | 78.5 |

*The chlorine content of the resin prepared is determined by assay of the chloride ions liberated by hydrolysis with sodium hydroxide. After the suspension has been acidified, the assay is performed using a silver-indicating electrode with a solution of silver nitrate.

EXAMPLE C

Preparation of poly(para-hydroxymethyl styrene)

1st stage:

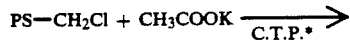

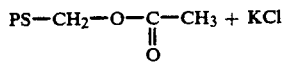

2nd stage:

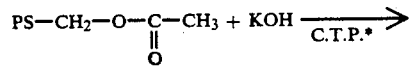

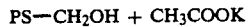

*PTC = phase transfer catalyst, consisting of tricaprylylmethylammonium chloride 10 g (55 meq) of PS—CH₂CL are placed in 70 ml (620 meq) of C₆H₄Cl₂ with stirring, for 1 hour. 15 g of CH₃COOK dissolved in 30 ml of water, and 3 ml of catalyst are added, and the round-bottomed flask is placed in an oil bath at 85–90° C. for approximately 30 hours; then, without performing a separation, 15 g of KOH, dissolved in 15 ml of water, and 1 ml of catalyst are added to the flask, and the mixture is left, still at the same temperature, for 45 hours. Next, the mixture is filtered with water, and then H₂O/tetrahydrofuran, mixtures with increasing concentrations of tetrahydrofuran, methanol and CH₂Cl₂.

Despite the heterogeneous-phase reaction, the reaction proceeds almost to completion.

EXAMPLE D

Preparation of poly(para-carboxymethyl styrene)

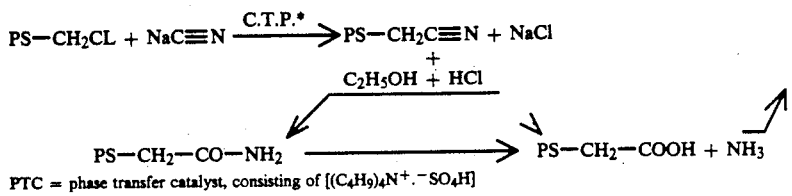

PTC = phase transfer catalyst, consisting of [(C₄H₉)₄N⁺.⁻SO₄H]

In a first step, 3.5 g of NaC≡N ar dissolved, in the heated state, in 50 ml of N,N-dimethylformamide, 5 g (26 meq) of PS—CH₂Cl, 50 ml of N,N-dimethylformamide and 1.2 g (3.5 meq) of [(C₄H₉)₄N⁺.⁻SO₄H] are added, the mixture is brought to 80° C. for 24 hours, it is next filtered, performing the traditional washes with H₂O, dioxane, methanol and CH₂Cl₂, and the resin formed, namely poly (paracyanomethylstyrene) PS—CH₂C≡N, is dried.

In a second step, 2 g (11 meq) of PS—CH₂—C≡N and a concentrated HCl (37.5 ml)/ethanol (12.5 ml) mixture are placed in a glass ampoule, which is sealed. The ampoule is brought to 110° C. for 30 hours, with agitation, and then, still with agitation, for 4 hours to room temperature; the ampoule (placed in an ice bath) is opened, and the mixture is again agitated at room temperature for 4 hours. The product obtained is immersed in a mixture of water and methanol; it is next filtered with increasing amounts of methanol; next, the product is placed for about 10 hours in suspension in 5N sodium hydroxide; it is filtered with water and then in 10⁻²N sodium hydroxide; the product is filtered with water (PS—CH₂—COONa is obtained). It is then left in suspension in a 3N HCl (50)/dioxane (50) mixture for about 10 hours, and filtrations are performed with H₂, dioxane, methanol and CH₂Cl₂.

EXAMPLE E

Preparation of poly(para-carboxyethyl styrene

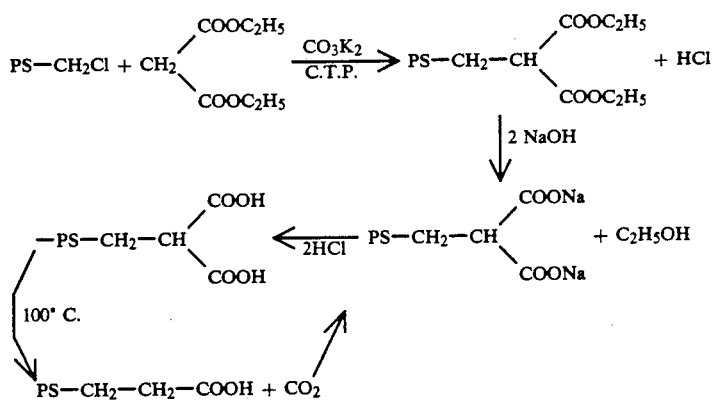

5 g of K₂CO₃ are dissolved, in the heated state, in 50 ml of N,N-dimethylformamide, and 1 g of tetrabutylammonium sulfate, 2 g (11 meq) of PS—CH₂Cl and 15 ml (100 meq) of (COOC₂H₅)₂CH₂ are then added, at 85° C., for 24 hours. The mixture is then filtered with water, tetrahydrofuran, methanol and CH₂Cl₂.

Next, 1 g of the diester obtained is placed with stirring in 15 ml of ethanol for 2 hours. 50 ml of 5N NaOH are added and the mixture is stirred for 15 hours. After filtration with water, the resin is suspended in 100 ml of 5N HCl, at 110° C., for 24 hours; it is then filtered with H$_2$O, dioxane, methanol and CH$_2$Cl$_2$.

EXAMPLE F1

Preparation of the compounds PS—(CH$_2$)$_{n=1,2}$—CH$_2$OH $$\tfrac{1}{2}B_2H_6 + 3H_2 + 3PS\text{-}(CH_2)_{\overline{n=1,2}}COOH \longrightarrow$$

$$3PS\text{-}(CH_2)_{\overline{n}}CH_2OH + B(OH)_3$$

This first method uses a molar commercial solution of B$_2$H$_6$ in tetrahydrofuran, and reacts at 0° C. to the extent of 95% according to the two reactions above.

After great care has been taken to dry everything beforehand, 0.8 g (3.5 meq) of PS—(CH$_2$)$_{1,2}$—COOH are placed in 35 ml of anhydrous tetrahydrofuran for 30 minutes; the round-bottomed flask is then placed in a bath at −5° C., −10° C., for 1 hour. Using a syringe, 18 ml of a 1M B$_2$H$_6$/tetrahydrofuran mixture are next injected slowly, still in the bath at the same temperature. The mixture is left with stirring for 1 hour; the flask is brought to 35° C. for 6 hours, and then to room temperature for about 30 hours. Finally, an H$_2$O (50)/tetrahydrofuran (50) mixture is added, and the resulting mixture is filtered with water and thereafter left with stirring in a solution (1N HCl, dioxane) for 15 hours; it is filtered and the product is suspended in 1N NaOH and then several times with 10$^{-2}$ NaOH for approximately 40 hours, and filtered with water, methanol and CH$_2$Cl$_2$.

EXAMPLE F2

Preparation of the compounds PS—(CH$_2$)$_{n=1,2}$—CH$_2$OH $$3NaBH_4 + 4BF_3 \longrightarrow 2B_2H_6 + 3NaBF_4 \quad \text{I}$$

$$\tfrac{1}{2}B_2H_6 + 3H_2 + 3PS\text{-}(CH_2)_{\overline{n=1,2}}COOH \longrightarrow \quad \text{II}$$

$$3PS\text{-}(CH_2)_{\overline{n}}CH_2OH + B(OH)_3$$

This second method requires the preparation of diborane "in situ", by the action of sodium borohydride (NaBH$_4$) on a mixture of boron trifluoride and 2-methoxyethyl ether ("diglyme"), in the presence of the resin PS—(CH$_2$)$_{n=1,2}$—COOH, according to the reactions I and II.

1 g (4 meq) of thoroughly dry resin is suspended in 20 ml of diglyme for 1 hour. 4.5 ml of a solution prepared by dissolving 1 g of NaBH$_4$ in 25 ml of diglyme (4.7 meq) are introduced using a phial. A solution of [0.75 ml (BF$_3$. (C$_2$H$_5$)$_2$—O), 1.25 ml diglyme] is next injected slowly. An H$_2$O (50)/diglyme (50) mixture is then added slowly using a dropping funnel. The mixture is poured into 200 ml of water. The product is filtered with water, dioxane, methanol and CH$_2$Cl$_2$.

EXAMPLE G

Preparation of poly[para-(N-hydroxyethylsulfamoyl)styrene and poly[para-(N-hydroxypropylsulfamoyl)styrene]

$$PS\text{—}SO_2Cl + H_2N\text{-}(CH_2)_{\overline{n=2,3}}OH \longrightarrow$$

$$PS\text{—}SO_2\text{—}NH\text{-}(CH_2)_{\overline{n=2,3}}OH + HCl$$

5.1 g (20 meq) of PS—SO$_2$Cl are placed in 50 ml of CH$_2$Cl$_2$ with stirring, for 1 hour. 28 ml (450 meq) of ethanolamine or 35 ml of propanolamine (450 meq), brought to 50° C., are added, for 24 hours. The mixture is next filtered with CH$_2$Cl$_2$ and with water. The product obtained is stirred for 2 hours in a 2N HCl ($\tfrac{1}{2}$)/H$_2$O ($\tfrac{1}{2}$) mixture; the resulting mixture is filtered and the product is thereafter stirred in water, tetrahydrofuran and CH$_2$Cl$_2$.

The yields are greater than 90%.

EXAMPLE H

Preparation of poly para-[N-(1,2-dihydroxypropyl)-sulfamoyl]styrene $$PS\text{—}SO_2Cl + H_2N\text{—}CH_2\text{—}CHOH\text{—}CH_2OH \longrightarrow$$

$$PS\text{—}SO_2\text{—}NH\text{—}CH_2\text{—}CHOH\text{—}CH_2OH + HCl$$

4 g (16 meq) of PS—SO$_2$Cl + 10 ml of CH$_2$Cl$_2$ + 8 ml (130 meq) of 3-amino-1,2-propanediol are placed at room temperature for 1 hour, and then at 50° C., with stirring, for 5 hours; and finally, at room temperature for 2 hours; the mixture is then filtered with CH$_2$Cl$_2$ and water; the product is stirred for 2 hours in HCl (0.3N) and filtered with water and CH$_2$Cl$_2$.

EXAMPLE I

Phosphorylation of the hydroxylated resins $$PS\text{—}SO_2\text{—}NH\text{—}(CH_2)_{\overline{2,3}}OH \longrightarrow$$

$$PS\text{—}SO_2\text{—}NH\text{—}(CH_2)_{\overline{2,3}}O\text{—}\underset{\underset{OH}{|}}{\overset{\overset{O}{\|}}{P}}\text{—}OH$$

$$PS\text{—}SO_2\text{—}NH\text{—}CH_2\text{—}\underset{\underset{OH}{|}}{CH}\text{—}CH_2OH \longrightarrow$$

$$PS\text{—}SO_2\text{—}NH\text{—}CH_2\text{—}\underset{\underset{OH}{|}}{CH}\text{—}CH_2\text{—}O\text{—}\underset{\underset{O}{\|}}{\overset{\overset{OH}{|}}{P}}\text{—}OH$$

$$PS\text{—}(CH_2)_{\overline{1,2,3}}OH \longrightarrow PS\text{—}(CH_2)_{\overline{1,2,3}}O\text{—}\underset{\underset{OH}{|}}{\overset{\overset{O}{\|}}{P}}\text{—}OH$$

A—Phosphorylation using methyl dichlorophosphate

The action of methyl dichlorophosphate on pyridine, followed by their action on an alcohol, has been described by J. SMURT and J. CATLIN in "Tetrahedron Letters", No. 58, pages 5081-82 (1970), and then by M. RUBINSTEIN and A. PATCHORNIK in "Tetrahedron Letters", vol. 31, pages 2107-2110 (1975). In a first stage, the N-methylpyridinium dichlorophosphate salt is formed, which thereafter reacts with an alcohol.

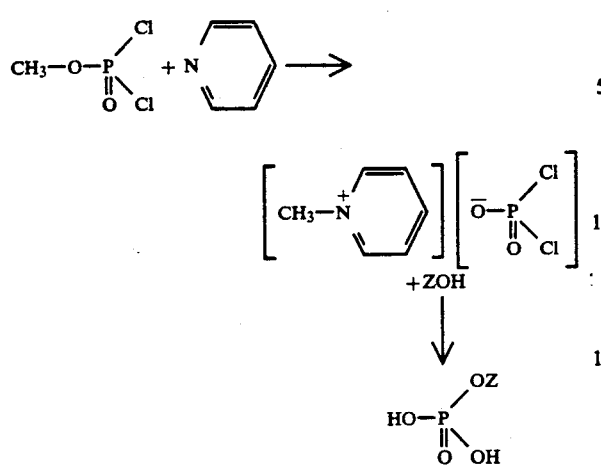

This method was performed on the two families of resins mentioned at the beginning of this example:

50 ml of anhydrous pyridine and 5 ml (50 meq) of methyl dichlorophosphate are placed at 0° C. for ½ hour. 2 g (approximately 10 meq) of the selected hydroxylated resin are introduced with stirring at room temperature, for 24 hours. The mixture is then poured into 400 ml of 10% strength NaHCO₃, with stirring, for 4 hours; the mixture is filtered; the product obtained is suspended in HCl (1N), the mixture is then filtered and the product is stirred in water, dioxane and $CH_2Cl_2$.

B—Phosphorylation using phosphorous acid

The principle of this method is based on the paper by H. TAKAKU, Y. SHIMADA and H. OKA, in "Chem. Pharm. Bull.", vol. 21, No. 8, pages 1844-45 (1973)', according to which phosphorous acid is used as a phosphorylating agent. The reaction can be split into two steps; in the first place, phosphorous acid $H_3PO_3$ on N-methylimidazole in the presence of mercuric chloride $HgCl_2$ forms the N-phosphoryl-N'-methylimidazole salt, which thereafter acts on an alcohol to form a substituted phosphate, that is to say:

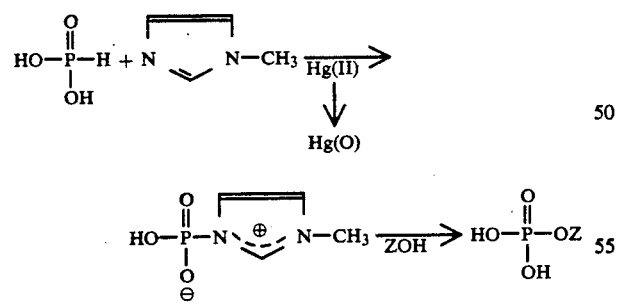

This method was performed on the two families of resins mentioned at the beginning of this example.

15 ml of N-methylimidazole (180 meq), 4.1 g (15 meq) of $HgCl_2$ and 1.5 g (15 meq) of $H_3PO_3$ are placed in a round-bottomed flask at 80° C. for 2 hours. 2 g (approximately 10 meq) of hydroxylated resin are added, still at 80° C., for 24 hours. The mixture is filtered with water, and the resulting mixture is poured into 400 ml of saturated sodium bicarbonate; the product is filtered with water, dioxane, methanol and $CH_2Cl_2$.

C—Phosphorylation using phosphorous oxychloride

The reaction may be represented thus:

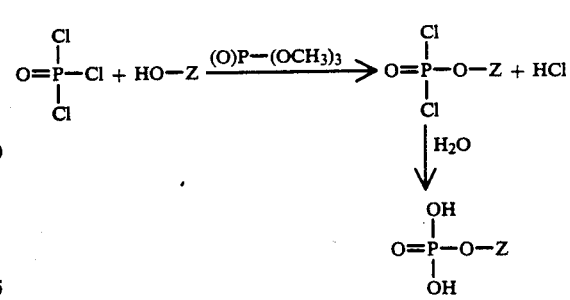

This method was performed on the three families of resins mentioned at the beginning of this example.

1 g (5 meq) of hydroxylated resin is mixed with 10 ml of PO—(OCH₃)₃ and with 1.5 g (10 meq) of POCl₃; the mixture is brought to 60° C. for 24 hours and then poured into water, and the product is washed with tetrahydrofuran, methanol and $CH_2Cl_2$.

The conversion of poly(hydroxyethylstyrene) to its phosphorylated compound, in which the desired groups

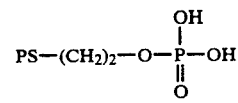

represent 78% of the mass of the resin, has been obtained, in particular.

EXAMPLE 2

A—Binding of uracil to chloromethylated polystyrene

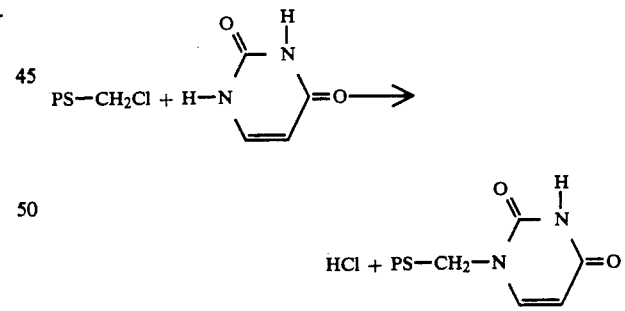

2 g (10.6 meq) of PS—CH₂Cl are placed in 20 ml of anhydrous dimethyl sulfoxide in a thoroughly dry round-bottomed flask with a CaCl₂ guard tube; 2.1 g (19 meq) of uracil, dissolved in the heated state in 30 ml of dimethyl sulfoxide, and 4.5 g of K₂CO₃ and 80 ml of dimethyl sulfoxide are added. The flask is brought to 40° C. under argon for 10 hours. The solution is poured into 600 ml of ice-cold water, which is stirred for 2 hours. The mixture is filtered with water, H₂O/tetrahydrofuran mixtures with increasing concentrations of tetrahydrofuran, methanol and $CH_2Cl_2$.

The degree of substitution of the polystyrene is 59%.

B—Binding of other bases to chloromethylated polystyrene

In the same manner as above, cytosine, thymine, adenine and guanine were bound to the PS—CH$_2$Cl resin, in dimethyl sulfoxide and in the presence of potassium carbonate, to obtain the following respective modified resins, the degrees of substitution of the polystyrene being, respectively, 53, 39, 74 and 89%:

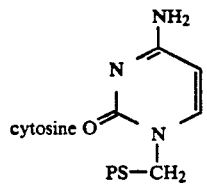 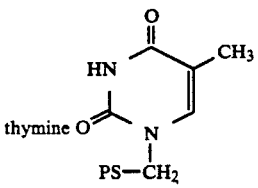

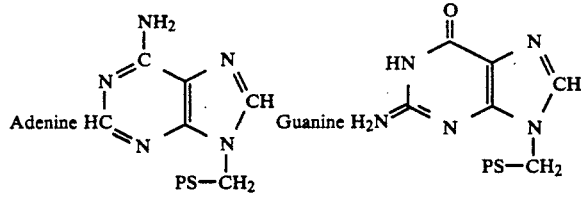

In addition, adenine was bound to the PS—CH$_2$Cl resin by conducting the reaction in ortho-dichlorobenzene, in the presence of potassium hydroxide.

EXAMPLE 3

Binding of bases to the

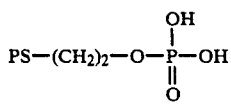

resin

N-Hydroxyethylated bases are prepared by reacting the chosen base with ethylene carbonate in the presence of the phase transfer catalyst [(C$_4$H$_9$)$_4$N$^\oplus$.$^\ominus$Br] in anhydrous N,N-dimethylformamide. It is easy to obtain the pure products by crystallization.

It is possible to condense these N-hydroxyethylated bases with the

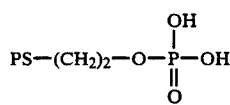

resin using N,N'-dicyclohexylcarbodiimide (DCCI), in N,N-dimethylformamide. The mechanism of action of DCCI is as follows:

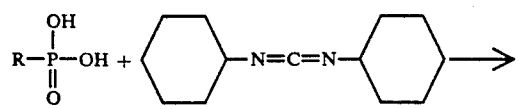

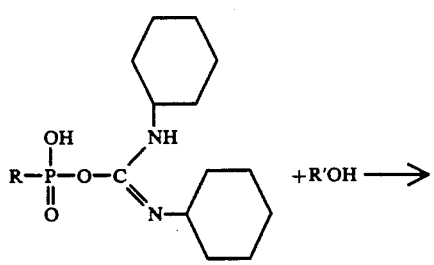

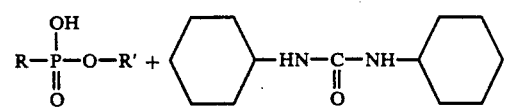

N,N'-Dicyclohexylurea is infinitely soluble in N,N-dimethylformamide and ethanol in the heated state.

When adenine is used as the base, the reaction scheme is as follows:

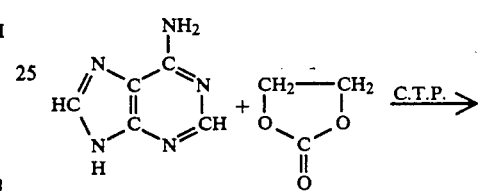

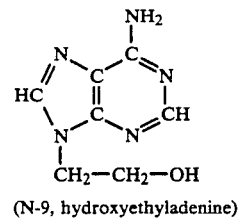

(N-9, hydroxyethyladenine)

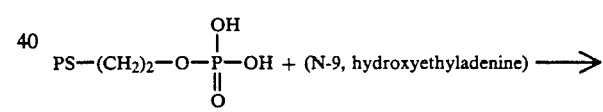

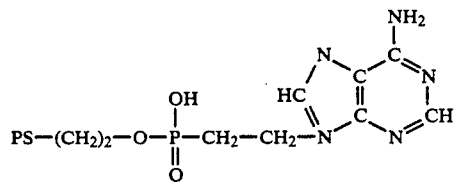

The condensation is carried out with 1 meq/g of "hydroxyethyl phosphate-hydroxyethyladenine" substitution (equivalent to 39% by mass) on the polystyrene, while leaving 0.9 meq/g of "hydroxyethyl phosphate" substitution (equivalent to 22% by mass).

When cytosine is used as the base, the first step is to prepare N$^1$-hydroxyethylcytosine of formula:

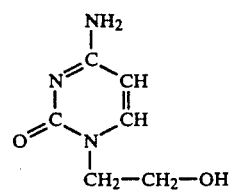

The condensation of N$^1$-hydroxyethylcytosine with

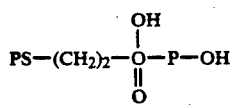

is carried out with 0.95 meq/g of "hydroxy-ethyl phosphate-hydroxyethylcytosine" substitution (equivalent to 34% by mass) on the polystyrene, while leaving 1.3 meq/g of "hydroxyethyl phosphate substitution (equivalent to 30% by mass).

When thymine is used as the base, the first step is to prepare N¹-hydroxyethylthymine of formula:

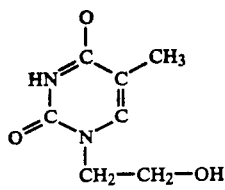

The condensation of N¹-hydroxyethylthymine with

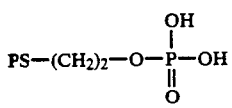

is carried out with 0.68 meq/g of "hydroxy-ethyl phosphate-hydroxyethylthymine" substitution (equivalent to 19% by mass) on the polystyrene, while leaving 1.8 meq/g of "hydroxyethyl phosphate" substitution (equivalent to 42% by mass).

EXAMPLE 4

Binding of hydroxyethylphosphate bases to poly(-parahydroxyethylstyrene)

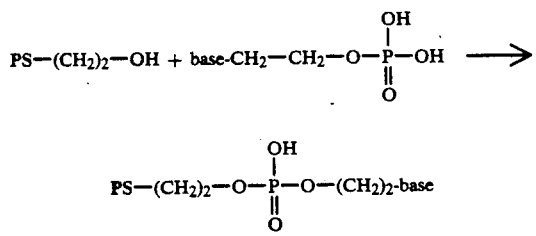

In the case where the base is adenine, the first step is to prepare N⁹-hydroxyethyladenine phosphate of formula:

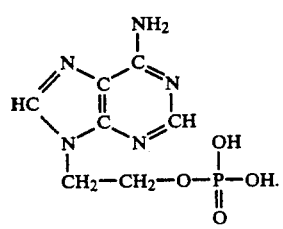

To this end, the phosphorylation of N⁹-hydroxyethyladenine is carried out with POCl₃, and the product obtained is then condensed with poly(hydroxyethylstyrene) using N,N'-dicyclohexylcarbodiimide, as described in Example 3.

1.03 meq/g of substitution (analysis identical with P or N) was thereby obtained, equivalent to 40% by mass of the molecule containing the phosphodiester and adenine, the remainder of the resin consisting of polystyrene substituted with hydroxyethyl and/or hydroxymethyl groups, and unsubstituted polystyrene.

EXAMPLE 5

Preparation of the Resin

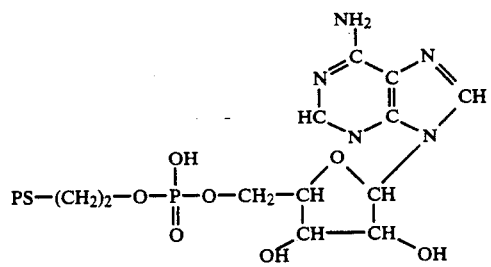

A: Binding of adenosine to the

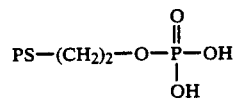

resin

The resin (2.5 meq) is allowed to swell in 18 ml of DMF. 1.3 g of adenosine and 10 ml of water are then added. The round-bottomed flask is brought to 105° C. for 2 and a half hours. After 2 evaporations under vacuum and resuspension in anhydrous DMF, 7 g of DCCI are added with 50 ml of anhydrous DMF, and the mixture is left for 18 hours at 110° C. The resin is successively washed with DMF and hot ethanol.

The condensation of the adenosine gives 0.34 meq/g of substitution (equivalent to 16.3%) and 2.54 meq/g of poly(hydroxyethyl phosphate)styrene (58%).

B: Binding of adenosine monophosphate to 

The procedure is the same as in Example 5 A, bringing 0.4 g of resin (2.4 meq) into contact with 0.9 g of adenosine monophosphate (2.6 meq).

An 8% substitution is thereby obtained with, accordingly, the same proportion of base, sugar and phosphate groups. The remainder of the resin consists of hydroxyl units.

TABLE III

| | | MICROANALYTICAL RESULTS | | | | | | | | | |
|---|---|---|---|---|---|---|---|---|---|---|---|
| Example | Resins | % C | % H | % O | % N | % Cl | % Na | % S | % P | meq/g | % Substitution* |
| | PS | 91.8 | 7.5 | 0.4 | <0.1 | <0.2 | | | | 9.5 | 98.5 |
| A | PS—CH$_2$Cl | 72 | 6.1 | | | 20.8 | | | | 5.9 | 90 |
| C | PS—CH$_2$CH | 79.4 | 7 | 10 | | 0.5 | | | | 6.3 | 84 |
| D (1st stage) | PS—CH$_2$—C≡N | 82.2 | 6.5 | 2 | 8.1 | <0.1 | | | | 5.8 | 83 |
| D (2nd stage) | PS—CH$_2$—COOH | 75.8 | 6.5 | 17.6 | ≦0.1 | <0.2 | | | | 5.5 | 89 |
| E (1st stage) | PS—CH$_2$—CH(COOC$_2$H$_5$)$_2$ | 73 | 17.1 | | | 0.4 | | | | 2.6 | 74 |
| E (2nd stage) | PS—(CH$_2$)$_2$—COOH | 74.1 | 6.9 | 16.4 | | | | | | 5.1 | 89 |
| G | PS—SO$_2$—NH—(CH$_2$)$_2$—OH | 50 | 5.8 | 25 | 5.21 | 0.5 | | 13.1 | | 3.7 | 84 |
| G | PS—SO$_2$—NH—(CH$_2$)$_3$—OH | 53 | 6.3 | 24 | 4.9 | <0.2 | | 12.8 | | 3.5 | 84 |
| H | PS—SO$_2$—NH—CH$_2$—CHOH—CH$_2$OH | 46.7 | 6 | 30 | 3.6 | <0.2 | | 12.6 | | 2.6 | 67 |
| F1 | PS—(CH$_2$)$_2$—OH | 80.6 | 7.9 | 9.6 | | 0.2 | | | | 6.0 | 88 |
| F2 | PS—(CH$_2$)$_3$—OH | 80.2 | 7.7 | 8.3 | | 0.3 | | | | 5.2 | 84 |
| 1 | PS—SO$_2$—NH—(CH$_2$)$_2$—O—P(O)(OH)$_2$ | 39.5 | 5 | 27.8 | 4.7 | 0.6 | | 10.1 | 7.8 | 2.5 | 77 |
| 1 | PS—CH$_2$—O—P(O)(OH)$_2$ | 66.3 | 6.9 | 16 | 2.4 | 0.7 | | | 4.3 | 1.4 | 30 |
| 1 | PS—(CH$_2$)$_2$—O—P(O)(OH)$_2$ | 53.8 | 6.5 | 24 | | 2.6 | | | 10.5 | 3.4 | 78 |
| 1 | PS—(CH$_2$)$_3$—O—P(O)(OH)$_2$ | 61.9 | 6.6 | 19.2 | | | | | 7.9 | 2.55 | 62 |
| 2 | PS—CH$_2$-guanine | 58.3 | 4.8 | 8.2 | 23.2 | 5.9 | | | | 3.3 | 89 |
| 2 | PS—CH$_2$-uracil | 71.8 | 5.7 | 13.1 | 7.2 | 1.9 | | | | 2.6 | 59 |
| 2 | PS—CH$_2$-thymine | 74.4 | 6.3 | 7 | 4.3 | | | | | 1.6 | 39 |
| 2 | PS—CH$_2$-cytosine | 70.4 | 6.4 | 8.8 | 9.8 | 3.4 | | | | 2.3 | 53 |
| 2 | PS—CH$_2$-adenine | 63.7 | 5.2 | | 20.7 | 5.2 | | | | 3 | 74 |
| | PS—(CH$_2$)—O—P(O)(OH)—O—W with W = | | | | | | | | | | |
| 3 | —(CH$_2$)-adenine | 58.2 | 7.2 | 18.3 | 7 | 0.3 | | | 6 | 1.0 | 39(and 20*—PO$_4$H$_2$) |
| 3 | —(CH$_2$)-cytosine | 59.3 | 6.9 | 19.6 | 3.9 | 0.4 | | | 6.8 | 0.93 | 34(and 29*—PO$_4$H$_2$) |
| 3 | —(CH$_2$)-thymine | 63 | 7 | 16.6 | 1.9 | | | | 7.05 | 0.68 | 19(and 36*—PO$_4$H$_2$) |
| 4 | —(CH$_2$)-adenine | 63.4 | 6.4 | 14.9 | 7.5 | 0.1 | | | 3.2 | 1.03 | 40 |
| 5 | —CH$_2$-(ribose)-adenine  A | 56.7 | 7 | 20.6 | 2.5 | 1.2 | | | 7.9 | 0.34 | 16(and 58*—PO$_4$H$_2$) |
| 5 | B | 76.1 | 7.5 | 12 | 11.8 | 0.48 | | | 0.48 | 0.17 | 8 |
| 6A | —CH$_2$—CH$_2$—N$^+$(CH$_3$)$_3$  a | 58.6 | 7.1 | 17.8 | 1.4 | 1.8 | | | 7.4 | 1.01 | 32 |
| | b | 56.6 | 7.8 | 20.1 | 2.5 | 1.9 | | | 5.45 | 1.8 | 56 |

TABLE III-continued

MICROANALYTICAL RESULTS

| Example | Resins | % C | % H | % O | % N | % Cl | % Na | % S | % P | meq/g | % Substitution* |
|---------|--------|-----|-----|-----|-----|------|------|-----|-----|-------|-----------------|
| 6B | —CH$_2$—CH(NH$_2$)(COOH) | 67.7 | 7 | 15.2 | 2.24 | 0.2 | | | 5.0 | 1.6 | 50 |

*The % by mass of sites substituted with the desired group are recorded here
*with respect to

EXAMPLE 6

Binding of phospholipid components

A—Binding of phosphocholine to poly(para-hydroxyethylstyrene)

$$PS-CH_2-CH_2-O-\overset{O^-}{\underset{\underset{O}{\|}}{P}}-O-CH_2-CH_2-\overset{+}{N}(CH_3)_3$$

a) First method

As described by H. J. LUCUS et al., J. Am. Chem. Soc. 72, p. 5491 (1950), the reaction of PCl$_3$ with ethylene glycol forms 2-chloro-1,3,2-dioxaphospholane; after oxidation in anhydrous benzene, 2-chloro-2-oxo-1,3,2-dioxaphospholane:

[structure of 2-chloro-2-oxo-1,3,2-dioxaphospholane]

is obtained.

This compound is then condensed at −10° C. in dichloromethane with a poly(hydroxyethyl styrene). The following unit is thereby obtained:

$$PS-(CH_2)_2-O-P(=O)(O-CH_2-CH_2-O)$$

This ring is then opened with a 20% strength solution of trimethylamine in THF, in order to obtain 1 meq/g of substitution (equivalent to 32%).

b) Second method

The same polymer can be produced by condensing poly(hydroxyethyl styrene) with bromoethyl dichlorophosphate, which is obtained by phosphorylation of bromoethanol with phosphorus oxychloride. The resulting phosphorylated polymer is then subjected to substitution by a trimethylamine solution; 1.8 meq/g of substitution (representing 56% of the mass of resin) are thus obtained.

B—Binding of the phosphoserine onto the poly(para-hydroxyethyl styrene)

$$PS-CH_2-CH_2-O-\overset{OH}{\underset{\underset{O}{\|}}{P}}-O-CH_2-\overset{NH_2}{CH}-COOH$$

The resin (5.5 meq) is allowed to swell in 30 ml of N,N'-dimethylformamide (DMF) for one hour. 1 gram of phosphoserine in 5 ml of water is then added. The suspension is heated to 100° C. for 2 hours. After two evaporations in vacuo and resuspension in anhydrous DMF, 10 g of DCCI in 20 ml of anhydrous DMF are added. After 18 hours at 110° C., the resin is washed with DMF and hot ethanol.

The condensation of the phosphoserine gives 1.6 meq/g of substitution (identical analysis for phosphorus and nitrogen), representing 50% of the mass of the resin.

EXAMPLE 7

Preparation of a phosphorylated carboxymethyl Sephadex ® resin

The basic Sephadex ® resin has the following chemical structure:

[chemical structure of Sephadex resin showing crosslinked dextran with carboxymethyl groups]

It results from the crosslinking, by epichlorohydrin, of a dextran of low plydispersity. It is here used in a form partly substituted by carboxymethyl groups.

First stage: Preparation of an aminohydroxylated carboxy-methyl-Sephadex ® resin Working method A: Formation of the acid chloride of the starting resin, followed by condensation with a hydroxylated amine.

10 g of crosslinked carboxymethyl-Sephadex ® (Pharmacia) —hereinafter referred to as CM Sephadex ®, containing 4 meq of COOH/g, are allowed to swell in 150 ml of benzene (solution 1). 4.5 ml of thionyl chloride are dissolved in 50 ml of benzene (solution 2). Solution 2 is slowly added to solution 1. The temperature of the reaction mixture is gradually raised to a value of 50-70° C. The reaction takes 24 hours. The product is filtered off and rapidly rinsed with dry benzene, after which it is suction-drained.

Thereafter, a condensation with ethanolamine is carried out in accordance with the following equation:

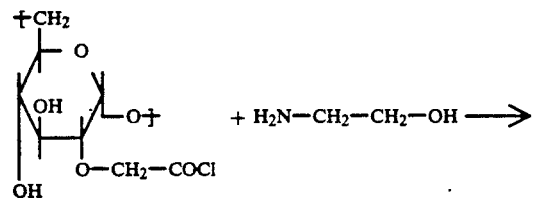

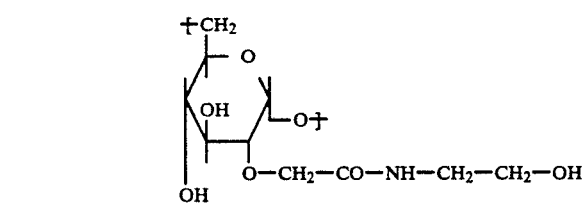

10 g of the acid chloride of CM Sephadex ®, corresponding to about 40 meq of chlorine, are suspended in 150 ml of pyridine. Ethanolamine, in a 3-fold molar excess relative to the acid chloride groups (namely, 7 ml), is then added to the reaction mixture (resin+pyridine), and the temperature is gradually raised to 70° C. it is kept at 35–40° C. for one hour, followed by heating at 72° C. for 24 hours. The product is filtered off, rinsed with water, washed with water to hydrolyze the residual chlorides, washed with H2O/ethanol solutions of increasing ethanol concentration and then suction-drained and dried in vacuo at 50° C. to constant weight.

Working method B: Coupling to N-ethoxycarbonyl-2-ethoxy-1,2-dihydroquinoline (EEDQ) followed by binding of a hydroxylated amine.

Stage 1: Coupling to EEDQ

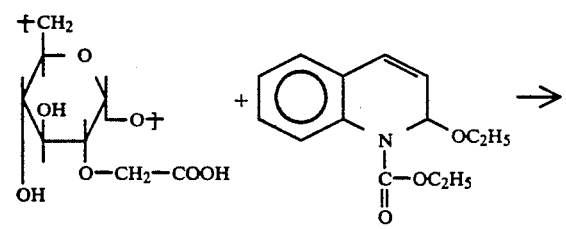

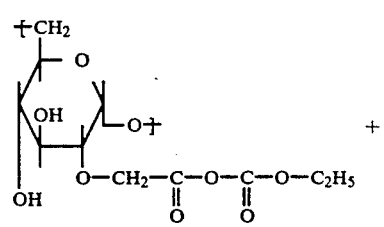

-continued

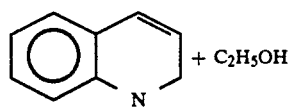 + C2H5OH 10 of crosslinked CM Sephadex ® are suspended in 70 ml of water. The pH is adjusted to 3 by addition of 1N HCl. Thereafter a solution of 20 g of EEDQ (corresponding to about 80 meq) in 160 ml of ethanol is added slowly. The reaction mixture must be left to stand, with stirring, for 30 minutes at ambient temperature.

Stage 2: Binding of the amine

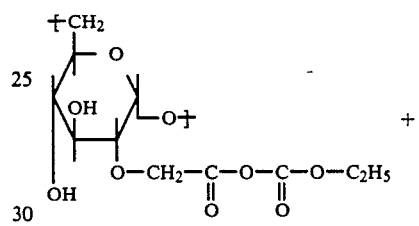

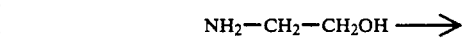

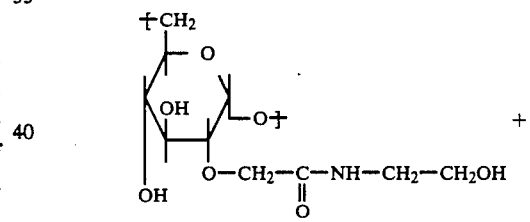

CO2 + C2H5OH 80 meq of ethanolamine are then added very slowly to the preceding reaction mixture (resin/H2O/EtOH-/EEDQ), with the stability of the pH being checked between successive additions. The pH is regulated to a value of about 9.3 throughout the duration of reaction, that is to say for hours at ambient temperature.

The product is filtered off and then washed with H2O/EtOH mixtures of increasing ethanol concentration (up to 100%), followed by methanol, before being suction-drained and then dried in vacuo at 50° C. to constant weight.

In these two working methods, the reaction can be carried out with other hydroxylated amines, such as propanolamine and hexanolamine, in which case the spacer arm will be different.

Second stage: Preparation of the title compound (phosphorylation similar to Example 1C)

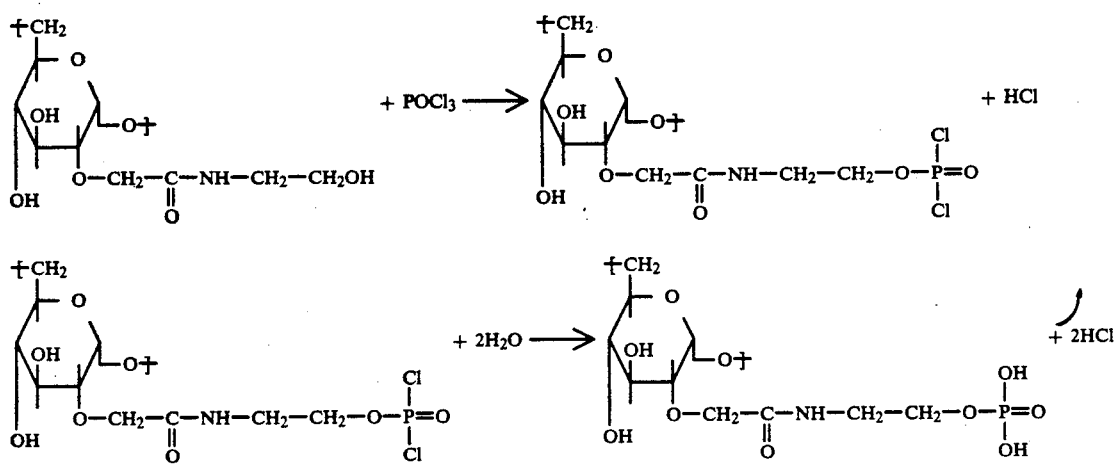
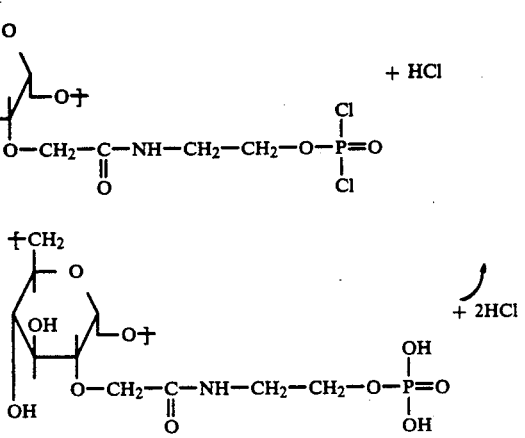

10 g of dry aminohydroxylated CM Sephadex® (containing 4 meq/g) are suspended in trimethyl phosphate, $PO(OCH_3)_3$. The resin is allowed to swell in the solvent for 1 to 2 hours at ambient temperature. Phosphorus oxychloride $POCl_3$ (45 meq) is then added to the resin-solvent mixture. The combination is heated to 60° C., the reaction time being 18 hours. The phosphorylated product is then hydrolyzed by addition of a few milliliters of water; it is then filtered off and washed with $H_2O$/dioxane mixtures of concentration ratio ½ and 2/1, and thereafter with pure dioxane and with methanol. The product obtained is then suction-drained and thereafter dried in vacuo at 50° C.

EXAMPLE 8

This example describes the titration curve which is shown in FIG. 1 and which is obtained with a

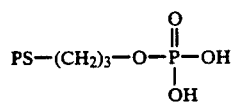

resin (substitution of phosphate group 60%), obtained in the same manner as in Examples F2 (as regards binding of the spacer arm) and 1 (as regards the phosphorylation). The titration product is sodium hydroxide. It is found that the pH zone which defines the optimum use conditions for this resin as an ion-exchange carrier is centered around pH 7. Under these conditions, such a resin favors the separation of proteins without danger of denaturing of the latter.

EXAMPLE 9

This example illustrates the application of the resin of Example 8 as a chromatographic support.

FIGS. 2 to 5 are chromatograms obtained using the resin of Example 8 in a stainless steel column 250×4 mm, with a high performance liquid chromatography system. The elution of the proteins is carried out either in 0.6M citrate buffer pH 5, or in 0.05M Tris buffer pH 7.6, at a flow rate of 0.1 or 0.2 ml/min.

Figure 6:
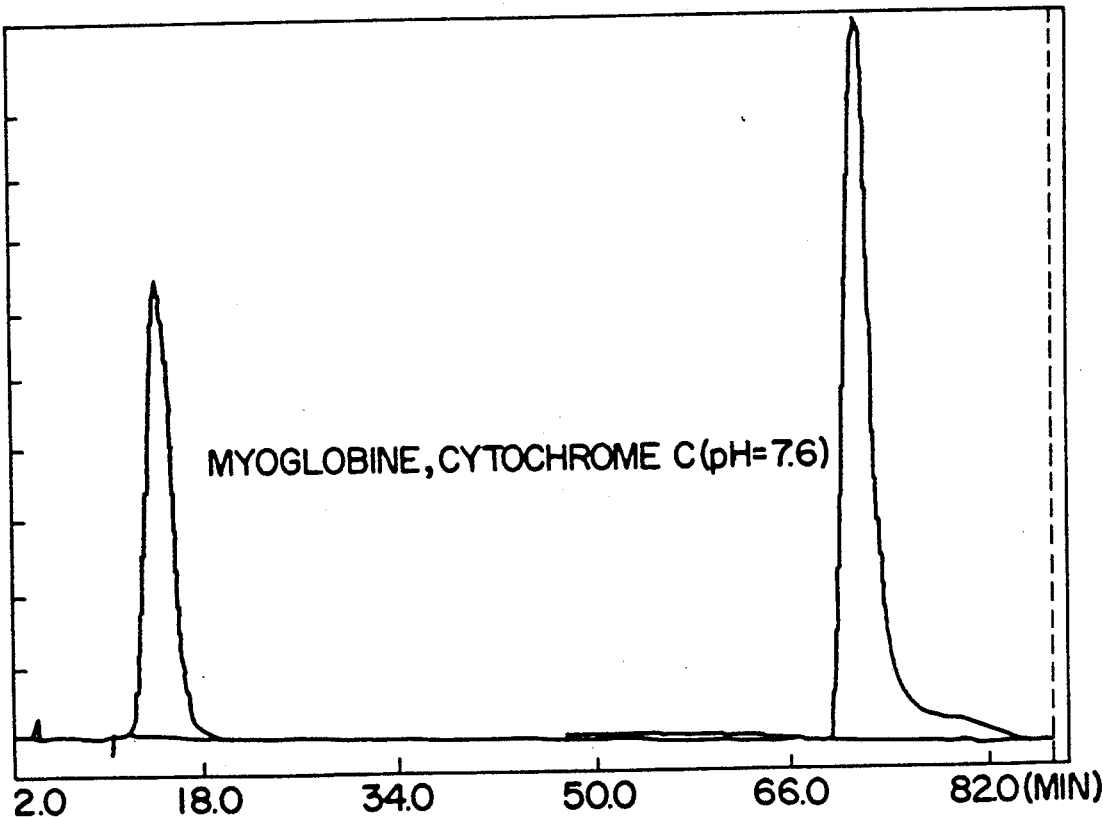

This resin enabled, in particular, a mixture consisting of myoglobin and cytochrome C to be separated by high performance liquid chromatography, as shown in FIG. 6.

Legends to the figures:

2: Cytochrome C in 0.16M citrate buffer pH 5, flow rate: 0.2 ml/min, elution time: 7.96 min 3: Cytochrome C in 0.05M Tris buffer, NaCl from 0 to 2M, pH 7.6, flow rate: 0.1 ml/min, elution time: 68.38 min 4: Ribonuclease in 0.16M citrate buffer, pH 5, flow rate: 0.2 ml/min, elution time: 8.53 min 5: Albumin in 0.16M citrate buffer, 2M NaCl, pH 5, flow rate: 0.1 ml/min, elution time: 18.5 min 6: Cytochrome C+myoglobin in 0.05M Tris buffer, pH 7.6, flow rate: 0.1 ml/min, NaCl from 0 to 2M, elution time: myoglobin=14.12 min; cytochrome C=71.06 min.

EXAMPLE 10

This example illustrates the use, as a specific immunoadsorbent, of the resin:

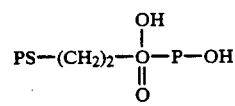

(substitution with phosphate groups: 70%) obtained in the same manner as in Examples F2 (for the binding of the spacer arm) and 1 (for the phosphorylation).

Figure 7:
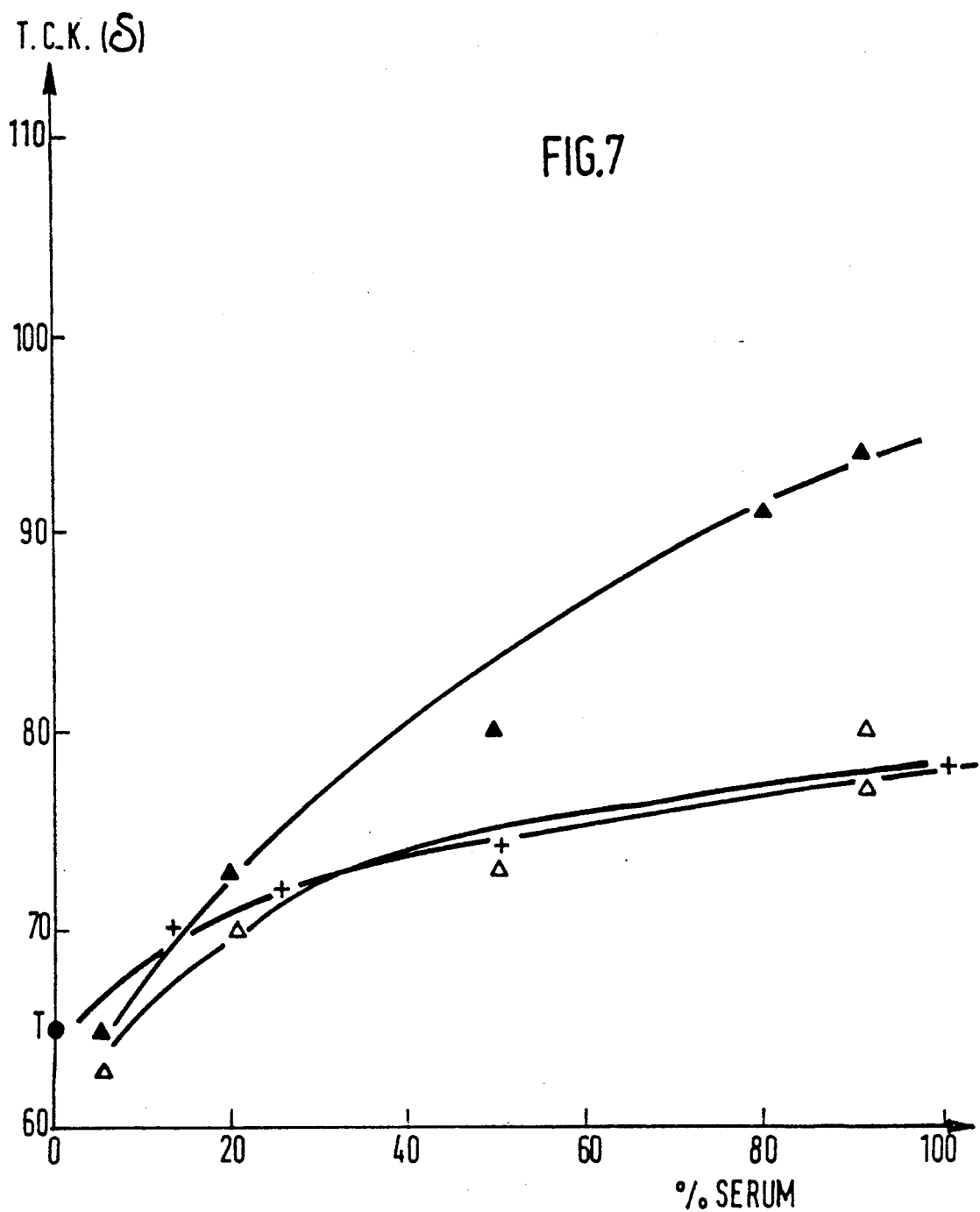
FIG. 7 shows the adsorption of circulating anticoagulants (CAC) from a lupous serum on resin bearing phosphate groups.

FIG. 7 shows the adsorption of circulating anticoagulants (CAC) from a lupous serum on a resin bearing phosphate groups. On the curve, the cephalin-kaolin time (CKT) in seconds is plotted as ordinates, and the dilution of the serum in the buffer as abscissae.

The prolongation of the coagulation time due to CAC no longer occurs if the lupous serum has been incubated beforehand with the resin. The curve is then identical to that for a normal human serum.

In FIG. 7:

▲: lupous serum

△: lupous serum incubated with the resin of the invention

+: normal human serum.

In addition, the content of anti-DNA antibodies in this serum, measured by the FARR test, has not changed, showing that the absorption of CAC on this resin is highly specific.

EXAMPLE 11

This example illustrates the use, as a specific immunoadsorbent, of the resin:

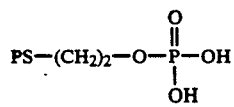

(substitution of phosphate groups: 30%), obtained in the same manner as in Example 10.

Figure 8:
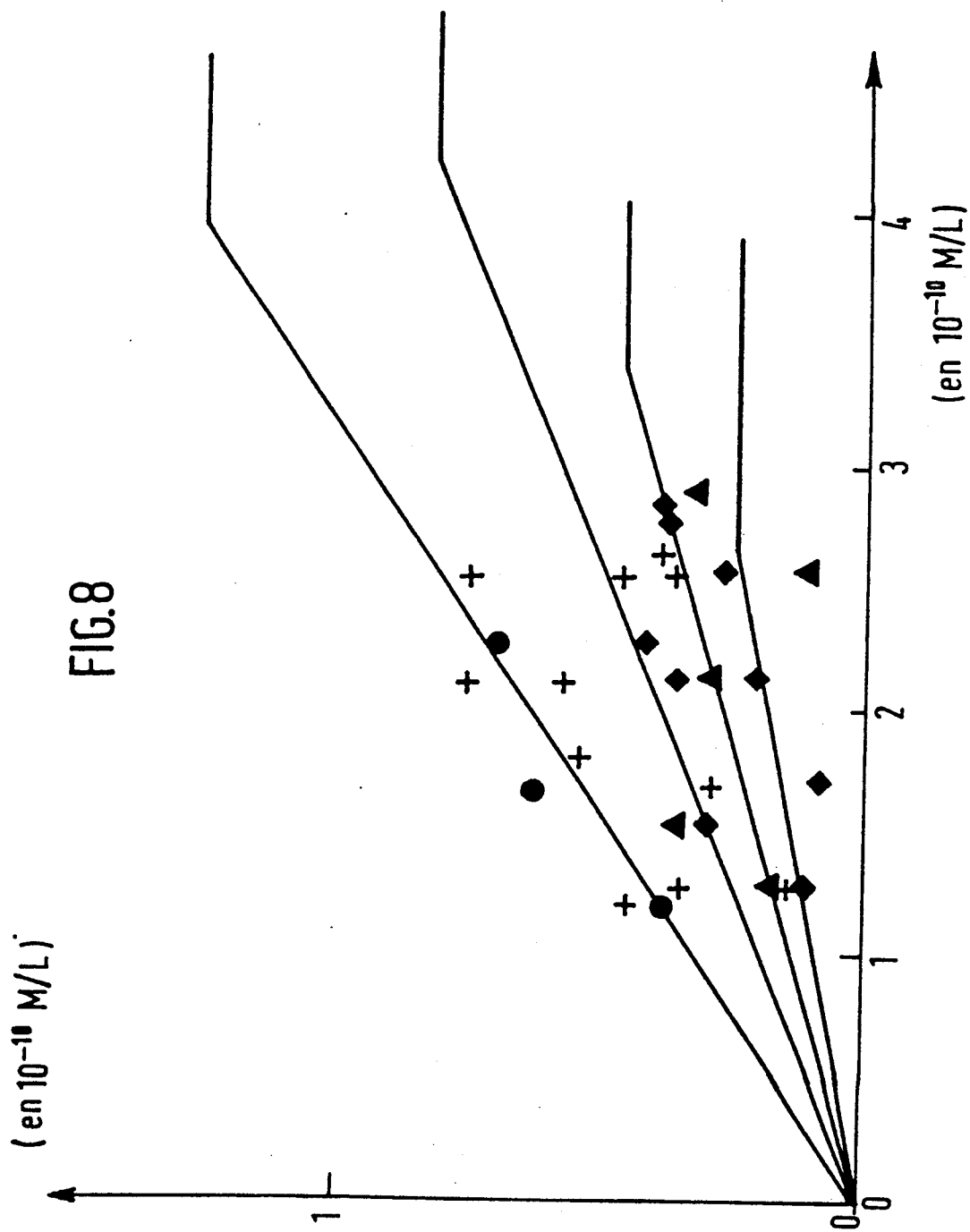
FIG. 8 shows the adsorption isotherms for anti-DNA IgG of a lupous serum on a resin bearing phosphate groups.

FIG. 8 shows the adsorption isotherm for anti-DNA IgG of a lupous serum on a resin bearing phosphate groups. On the curves, the molar concentrations of anti-DNA IgG adsorbed on the resin at equilibrium are plotted as ordinates, and the concentration of the same IgG molecules in the lupous serum as abscissae, for different quantities of polymer suspended in the serum.

In FIG. 8:
- ●: 322 g of polymer per 1 of serum
- +: 215 g
- ↕: 107 g
- ▲: 54 g

EXAMPLE 12

This example illustrates the use, as a stationary phase in affinity chromatography, of the resin:

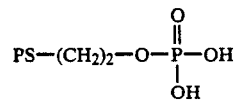

(substitution with phosphate groups: 64%), obtained in the same manner as in Example 10, for the purification of an RNA polymerase B factor required for the transcription of DNA.

In this example, a cell extract containing the UEF transcription factor for the major late promoter of adeno-virus-2 and other biological polymers, dissolved in a 50 mM Tris-HCl buffer at pH 7.9, 50 mM KCl, is deposited at 4° C. on a chromatographic column consisting of 300 μl of the resin, equilibrated beforehand in the same buffer.

An elution performed with a 50 mM Tris-HCl buffer at pH 7.9, 1M KCl solution enables the UEF factor to be obtained in a high degree of purity. The characterization of the factor is performed by two methods:
- polyacrylamide gel electrophoresis, which reveals the presence of the purified UEF factor;
- demonstration of the biological activity of the UEF factor, according to the method described by V. Moncollin et al., Embo Journal, vol. 5, page 2577-2584 (1986).

This example demonstrates that the resin specifically binds the UEF factor to the exclusion of the other constituents of the transcription complex which are, nevertheless, present in the initial cell extract, and illustrates the possibilities of use of the resin in affinity chromatography for the purification of polymers of biological origin.

EXAMPLE 13

This example illustrates the use of phosphorylated polystyrenes, obtained in the same manner as in Example 10, as a specific immunoadsorbent.

Figure 9:
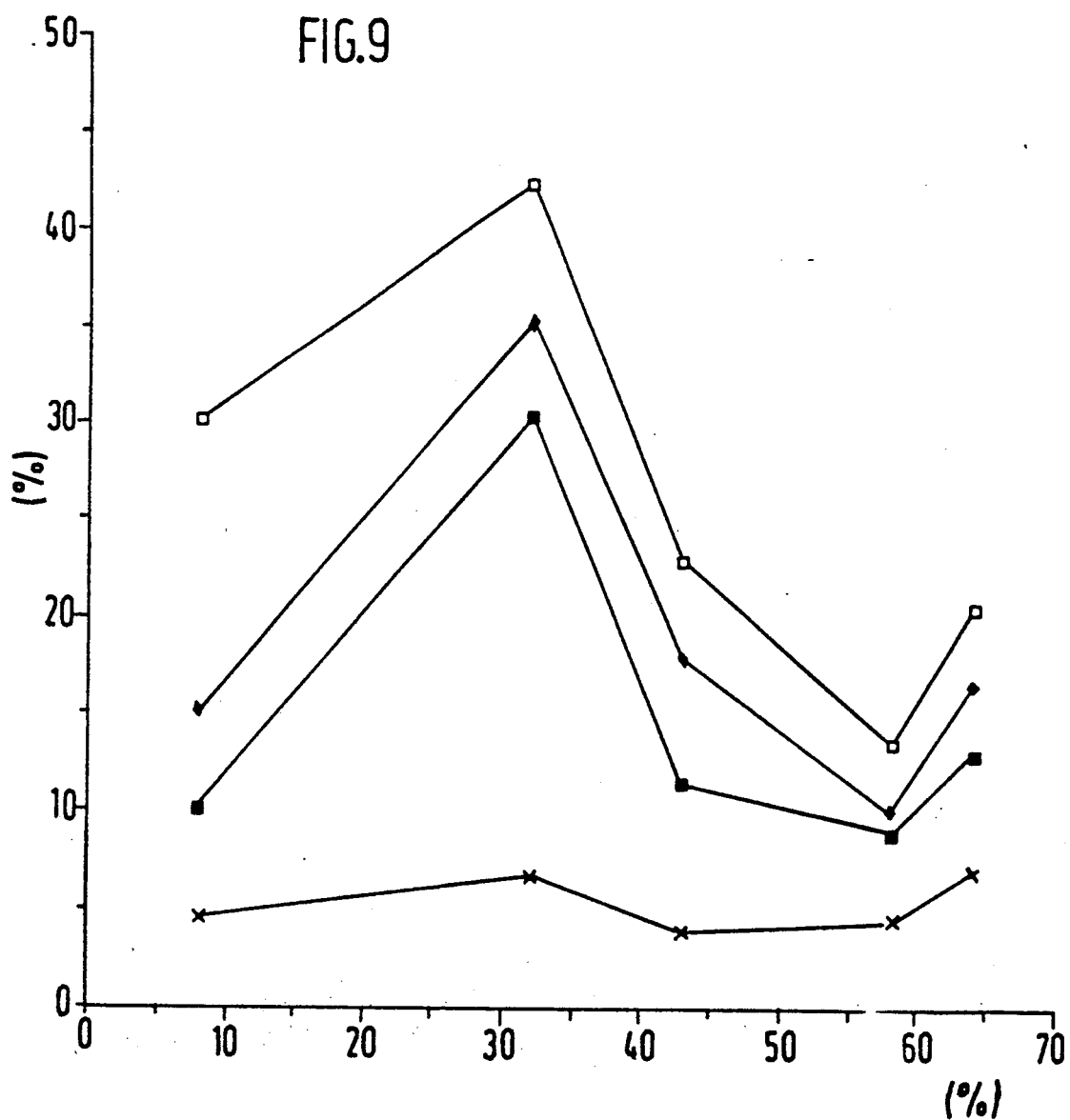
FIG. 9 represents the adsorption of the anti-DNA antibodies from a lupous system at four dilutions onto phosphorylated polystyrenes having different degrees of substitution with phosphate groups.

FIG. 9 represents the adsorption of the anti-DNA antibodies from a lupous serum at four dilutions onto phosphorylated polystyrenes having different degrees of substitution with phosphate groups.

Legend to FIG. 9:

Abscissae: degree of substitution with phosphate groups (%)

Ordinates: percentage of anti-DNA antibodies adsorbed
- □: 100% serum
- ↕: 80% serum
- ■: 60% serum
- ✗: 40% serum The results obtained indicate that there is an optimum phosphate content (around 30%) for the specific adsorption of the anti-DNA antibodies onto this type of resin.

EXAMPLE 14

This example illustrates the use of the synthesized polymers as carriers for the determination of antibodies.

In this example, the resins obtained in the same manner as in Example 10 (58, 64 and 71% substitution) are incubated for ½ hour at 4° C. with three categories of plasma: the first consists of normal human plasma; the second, of lupous plasma containing circulating anticoagulants (CAC); and the last, lupous plasma with anti-DNA antibodies.

After centrifuging, removal of the supernatant liquor and washing of the polymers with an 0.1M borate buffer containing 0.2% of bovine albumin serum (BAS) (pH=8.4), a solution of human anti-Fc antibodies radiolabeled with iodine 125 is added to the resin. After 4 hours at 4° C. with stirring, the same washing operations as above are carried out. The resin is then introduced into a gamma counter.

The amounts of human anti-Fc antibodies fixed to the resins are thus greater in the case of the incubations with lupous plasma (FIG. 10), especially with those containing CAC. This confirms clearly that the lupous antibodies are specifically adsorbed by their Fab fragment, thus leaving their Fc fragment free.

It is thus possible directly to quantify the specifically fixed antibodies. Furthermore, the determination of the antibodies present in the plasma of lupus patients is thus effected with the aid of these resins.

Figure 10:
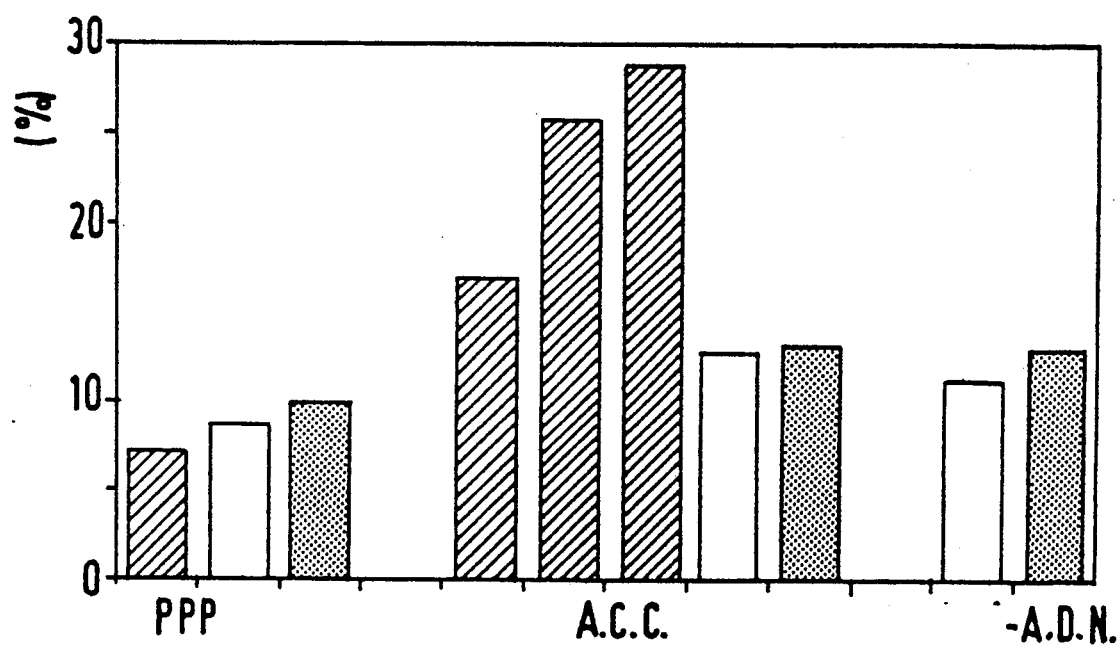
FIG. 10 shows the fixation on different resins of anti-$F_c$ antibodies from normal human plasma, lupous plasma containing CAC lupous plasma with anti-DNA antibodies.

Legend to FIG. 10:

Ordinates: percentage of anti-Fc IgG adsorbed
- ▨: resin containing 71% of phosphate groups
- □: resin containing 58% of phosphate groups
- ▨: resin containing 64% of phosphate groups

What is claimed is:

1. In a process of ion-exchange chromatography, the improvement comprising using as a stationary phase a base polymer selected from the group consisting of a crosslinked styrene polymer or copolymer, or a crosslinked dextran, in which chains of the base polymer or copolymer are substituted with one or more groups, which may be identical or different, belonging to the following categories:

—Z—$A_1$;
—Z—$A_2$;
—Z—$A_1$—Z'—$A_2$;
—Z—$A_1$—$A_3$—$A_2$;
—Z—$A_1$—$A_4$ wherein Z and Z' are chosen from the following moieties;

—(CH$_2$)—$_n$, n being 1 to 12, optionally made hydrophilic by the replacement of at least one H by an OH; or —O—(CH$_2$)—$_r$, r being 0 to 12, optionally being made hydrophilic by the replacement of at least one H by an OH; or —SO$_2$NH—(CH$_2$)—$_m$, m being 1 to 12, the moiety —(CH$_2$)$_m$—, optionally being made hydrophilic by the replacement of at least one H by an OH; and in the case of the modification of a crosslinked dextran, also

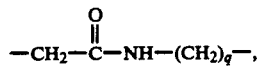

q being 1 to 12, the residue —(CH$_2$)q— optionally being made hydrophilic by the replacement of at least one H by an OH;

A$_1$ denotes a phosphorylated moiety

A$_2$ denotes a chemical moiety derived from a purine base or a pyrimidine base;

A$_3$ denotes a chemical group derived from a sugar; and

A$_4$ denotes a moiety of a molecule participating in the polar structure of a phospholipid.

2. The process of claim 1 wherein enzymes, coenzymes or enzyme complexes accepting DNA, RNA and nucleotides as substituents are purified.

3. The process of claim 1 wherein plasma extracts of blood coagulation factors are purified.

4. The process of claim 1 wherein proteins participating in blood coagulation are purified.

5. The process of claim 1 wherein different types of lupous antibodies are determined.

6. The process of claim 1 wherein different types of lupous antibodies are determined.

7. In a process of affinity chromatography, the improvement comprising using as a stationary phase a base polymer selected from the group consisting of a crosslinked styrene polymer or copolymer, or a crosslinked dextran, in which chains of the base polymer or copolymer are substituted with one or more groups, which may be identical or different, belonging to the following categories:

—Z—A$_1$;
—Z—A$_2$;
—Z—A$_1$—Z'—A$_2$;
—Z—A$_1$—A$_3$—A$_2$;
—Z—A$_1$—A$_4$ wherein Z and Z' are chosen from the following moieties;

—(CH$_2$)—$_n$, n being 1 to 12, optionally made hydrophilic by the replacement of at least one H by an OH; or —O—(CH$_2$)—$_r$, r being 0 to 12, optionally being made hydrophilic by the replacement of at least on H by an OH; or —SO$_2$NH—(CH$_2$)$_m$—, m being 1 to 12, moiety —(CH$_2$)$_m$—optionally being made hydrophilic by the replacement of at least one H by an OH; and in the case of the modification of a crosslinked dextran, also

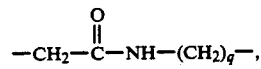

q being 1 to 12, the residue —(CH$_2$)q— optionally being made hydrophilic by the replacement of at least one H by an OH;

A$_1$ denotes a phosphorylated moiety

A$_2$ denotes a chemical moiety derived from a purine base or a pyrimidine base;

A$_3$ denotes a chemical group derived from a sugar; and

A$_4$ denotes a moiety of a molecule participating in the polar structure of a phospholipid.

8. The process of claim 7 wherein different types of antibodies developed by lupous patients are selectively purified.

9. The process of claim 7 wherein enzymes, coenzymes or enzyme complexes accepting DNA, RNA and nucleotides as substituents are purified.

10. The process of claim 7 wherein plasma extracts of blood coagulation factors are purified.

11. The process of claim 7 wherein proteins participating in blood coagulation are purified.

12. The process of claim 7 wherein different types of circulating anticoagulants and/or antiphosolipids are determined.

* * * * *